(12) United States Patent
Kelly et al.

(10) Patent No.: US 11,311,304 B2
(45) Date of Patent: Apr. 26, 2022

(54) ACTUATED CLOT RETRIEVAL CATHETER

(71) Applicant: Neuravi Limited, Galway (IE)

(72) Inventors: Ronald Kelly, Galway (IE); Karl Keating, Galway (IE)

(73) Assignee: Neuravi Limited, Galway (IE)

( * ) Notice: Subject to any disclaimer, the term of this patent is extended or adjusted under 35 U.S.C. 154(b) by 0 days.

(21) Appl. No.: 16/809,085

(22) Filed: Mar. 4, 2020

(65) Prior Publication Data
US 2020/0281611 A1  Sep. 10, 2020

Related U.S. Application Data

(60) Provisional application No. 62/813,723, filed on Mar. 4, 2019.

(51) Int. Cl.
*A61B 17/221* (2006.01)
*A61B 17/00* (2006.01)

(52) U.S. Cl.
CPC .. *A61B 17/221* (2013.01); *A61B 2017/00867* (2013.01); *A61B 2017/2212* (2013.01)

(58) Field of Classification Search
CPC . A61B 17/22; A61B 17/221; A61B 17/22031; A61B 2017/22031; A61B 2017/22035; A61B 2017/2212; A61B 2017/2217
See application file for complete search history.

(56) References Cited

U.S. PATENT DOCUMENTS

| 4,243,040 A | 1/1981 | Beecher |
| 4,324,262 A | 4/1982 | Hall |
| 4,351,342 A | 9/1982 | Wiita et al. |
| 4,575,371 A | 3/1986 | Nordqvist et al. |

(Continued)

FOREIGN PATENT DOCUMENTS

| CN | 1972728 A | 5/2007 |
| CN | 103071195 A | 5/2013 |

(Continued)

OTHER PUBLICATIONS

US 6,348,062 B1, 02/2002, Hopkins (withdrawn)
(Continued)

*Primary Examiner* — Martin T Ton
(74) *Attorney, Agent, or Firm* — Troutman Pepper Hamilton Sanders LLP

(57) ABSTRACT

Devices described herein include an actuated clot retrieval catheter system. The system includes a catheter having a frame disposed proximate the distal end of the catheter. The frame expands to form a seal with the inner wall of a vessel. In some examples, the frame also captures a clot for removal from the vessel. The frame is manufactured from a shape memory material that can be heat set into a predetermined shape. An electrical connection to an electronic circuit causes a current to run through the frame. The electrical resistance of the shape memory material causes the frame to heat and transition from a martensite to an austenite phase. When the frame is heat set into an expanded configuration, the current causes the frame heat and expand. When the frame is heat set into a closed configuration, the current causes the frame heat and collapse upon a clot.

9 Claims, 20 Drawing Sheets

(56) References Cited

U.S. PATENT DOCUMENTS

| | | |
|---|---|---|
| 4,719,924 A | 1/1988 | Crittenden et al. |
| 4,738,666 A | 4/1988 | Fuqua |
| 4,767,404 A | 8/1988 | Renton |
| 4,793,348 A | 12/1988 | Palmaz |
| 4,873,978 A | 10/1989 | Ginsburg |
| 5,011,488 A | 4/1991 | Ginsburg |
| 5,092,839 A | 3/1992 | Kipperman |
| 5,102,415 A | 4/1992 | Guenther et al. |
| 5,122,136 A | 6/1992 | Guglielmi et al. |
| 5,123,840 A | 6/1992 | Nates |
| 5,171,233 A | 12/1992 | Amplatz |
| 5,234,437 A | 8/1993 | Sepetka |
| 5,256,144 A | 10/1993 | Kraus et al. |
| 5,372,124 A * | 12/1994 | Takayama ............ B25J 15/0206 600/106 |
| 5,385,562 A | 1/1995 | Adams |
| 5,387,219 A | 2/1995 | Rappe |
| 5,387,226 A | 2/1995 | Miraki |
| 5,396,902 A | 3/1995 | Brennen et al. |
| 5,449,372 A | 9/1995 | Schmaltz |
| 5,520,651 A | 5/1996 | Sutcu |
| 5,538,512 A | 7/1996 | Zenzon et al. |
| 5,549,626 A | 8/1996 | Miller et al. |
| 5,558,652 A | 9/1996 | Henke |
| 5,609,627 A | 3/1997 | Goicoechea et al. |
| 5,624,461 A | 4/1997 | Mariant |
| 5,639,277 A | 6/1997 | Mariant |
| 5,645,558 A | 7/1997 | Horton |
| 5,658,296 A | 8/1997 | Bates |
| 5,662,671 A | 9/1997 | Barbut |
| 5,695,519 A | 12/1997 | Summer et al. |
| 5,709,704 A | 1/1998 | Nott et al. |
| 5,713,853 A | 2/1998 | Clark |
| 5,728,078 A | 3/1998 | Powers, Jr. |
| 5,769,871 A | 6/1998 | Mers Kelly |
| 5,779,716 A | 7/1998 | Cano |
| 5,810,874 A | 9/1998 | Lefebvre |
| 5,814,064 A | 9/1998 | Danniel et al. |
| 5,827,304 A | 10/1998 | Hart |
| 5,855,598 A | 1/1999 | Pinchuk |
| 5,893,869 A | 4/1999 | Barnhart et al. |
| 5,895,398 A | 4/1999 | Wensel |
| 5,897,567 A | 4/1999 | Ressemann |
| 5,904,698 A | 5/1999 | Thomas et al. |
| 5,911,725 A | 6/1999 | Boury |
| 5,935,139 A | 8/1999 | Bates |
| 5,938,645 A | 8/1999 | Gordon |
| 5,947,995 A | 9/1999 | Samuels |
| 5,968,057 A | 10/1999 | Taheri |
| 5,971,938 A | 10/1999 | Hart et al. |
| 5,997,939 A | 12/1999 | Moechnig et al. |
| 6,063,113 A | 5/2000 | Kavteladze |
| 6,066,149 A | 5/2000 | Samson et al. |
| 6,066,158 A | 5/2000 | Engelson |
| 6,093,196 A | 7/2000 | Okada |
| 6,093,199 A | 7/2000 | Brown et al. |
| 6,096,053 A | 8/2000 | Bates |
| 6,099,534 A | 8/2000 | Bates |
| 6,102,932 A | 8/2000 | Kurz |
| 6,106,548 A | 8/2000 | Roubin et al. |
| 6,129,739 A | 10/2000 | Khosravi |
| 6,146,396 A | 11/2000 | Konya et al. |
| 6,146,404 A | 11/2000 | Kim |
| 6,165,194 A | 12/2000 | Denardo |
| 6,165,199 A | 12/2000 | Barbut |
| 6,168,604 B1 | 1/2001 | Cano |
| 6,168,622 B1 | 1/2001 | Mazzocchi |
| 6,174,318 B1 | 1/2001 | Bates et al. |
| 6,179,861 B1 | 1/2001 | Khosravi |
| 6,203,561 B1 | 3/2001 | Ramee |
| 6,214,026 B1 | 4/2001 | Lepak |
| 6,221,006 B1 | 4/2001 | Dubrul |
| 6,238,412 B1 | 5/2001 | Dubrul |
| 6,245,087 B1 | 6/2001 | Addis |
| 6,251,122 B1 | 6/2001 | Tsukernik |
| 6,254,571 B1 | 7/2001 | Hart |
| 6,264,663 B1 | 7/2001 | Cano |
| 6,306,163 B1 | 10/2001 | Fitz |
| 6,309,379 B1 | 10/2001 | Willard |
| 6,312,444 B1 | 11/2001 | Barbut |
| 6,315,778 B1 | 11/2001 | Gambale et al. |
| 6,325,819 B1 | 12/2001 | Pavcnik et al. |
| 6,334,864 B1 | 1/2002 | Amplatz et al. |
| 6,336,934 B1 | 1/2002 | Gilson et al. |
| 6,348,056 B1 | 2/2002 | Bates |
| 6,350,271 B1 | 2/2002 | Kurz et al. |
| 6,361,545 B1 | 3/2002 | Macoviak |
| 6,375,668 B1 | 4/2002 | Gifford et al. |
| 6,383,205 B1 | 5/2002 | Samson et al. |
| 6,383,206 B1 | 5/2002 | Gillick |
| 6,391,037 B1 | 5/2002 | Greenhalgh |
| 6,402,771 B1 | 6/2002 | Palmer |
| 6,409,683 B1 | 6/2002 | Fonseca et al. |
| 6,416,541 B2 | 7/2002 | Denardo |
| 6,425,909 B1 | 7/2002 | Dieck et al. |
| 6,432,122 B1 | 8/2002 | Gilson et al. |
| 6,436,112 B2 | 8/2002 | Wensel |
| 6,458,139 B1 | 10/2002 | Palmer |
| 6,346,116 B1 | 11/2002 | Brooks et al. |
| 6,485,497 B2 | 11/2002 | Wensel |
| 6,485,501 B1 | 11/2002 | Green |
| 6,485,502 B2 | 11/2002 | Don Michael |
| 6,511,492 B1 | 1/2003 | Rosenbluth |
| 6,517,551 B1 | 2/2003 | Driskill |
| 6,520,934 B1 | 2/2003 | Lee et al. |
| 6,520,951 B1 | 2/2003 | Carrillo, Jr |
| 6,530,935 B2 | 3/2003 | Wensel |
| 6,530,939 B1 | 3/2003 | Hopkins |
| 6,540,768 B1 | 4/2003 | Diaz et al. |
| 6,544,279 B1 | 4/2003 | Hopkins |
| 6,551,341 B2 | 4/2003 | Boylan et al. |
| 6,551,342 B1 | 4/2003 | Shen et al. |
| 6,575,997 B1 | 6/2003 | Palmer et al. |
| 6,582,448 B1 | 6/2003 | Boyle |
| 6,585,756 B1 | 7/2003 | Strecker |
| 6,589,265 B1 | 7/2003 | Palmer et al. |
| 6,592,607 B1 | 7/2003 | Palmer et al. |
| 6,592,616 B1 | 7/2003 | Stack |
| 6,602,271 B2 | 8/2003 | Adams |
| 6,602,272 B2 | 8/2003 | Boylan et al. |
| 6,605,102 B1 | 8/2003 | Mazzocchi et al. |
| 6,610,077 B1 | 8/2003 | Hancock et al. |
| 6,616,679 B1 | 9/2003 | Khosravi |
| 6,632,241 B1 | 10/2003 | Hanoock et al. |
| 6,638,245 B2 | 10/2003 | Miller |
| 6,638,293 B1 | 10/2003 | Makower et al. |
| 6,641,590 B1 | 11/2003 | Palmer et al. |
| 6,652,555 B1 | 11/2003 | VanTassel et al. |
| 6,656,218 B1 | 12/2003 | Denardo et al. |
| 6,660,021 B1 | 12/2003 | Palmer et al. |
| 6,663,650 B2 | 12/2003 | Sepetka |
| 6,673,089 B1 | 1/2004 | Yassour et al. |
| 6,685,722 B1 | 2/2004 | Rosenbluth |
| 6,692,504 B2 | 2/2004 | Kurz et al. |
| 6,692,508 B2 | 2/2004 | Wensel |
| 6,692,509 B2 | 2/2004 | Wensel |
| 6,702,782 B2 | 3/2004 | Miller |
| 6,712,834 B2 | 3/2004 | Yassour et al. |
| 6,726,701 B2 | 4/2004 | Gilson et al. |
| 6,730,104 B1 | 5/2004 | Sepetka |
| 6,726,703 B2 | 8/2004 | Broome et al. |
| 6,824,545 B2 | 11/2004 | Sepetka |
| 6,855,155 B2 | 2/2005 | Denardo et al. |
| 6,878,163 B2 | 4/2005 | Denardo et al. |
| 6,890,340 B2 | 5/2005 | Duane |
| 6,913,612 B2 | 7/2005 | Palmer |
| 6,913,618 B2 | 7/2005 | Denardo et al. |
| 6,953,472 B2 | 10/2005 | Palmer et al. |
| 6,989,019 B2 | 1/2006 | Mazzocchi |
| 6,989,021 B2 | 1/2006 | Bosma et al. |
| 6,994,718 B2 | 2/2006 | Groothuis et al. |
| 6,997,939 B2 | 2/2006 | Linder |
| 7,004,954 B1 | 2/2006 | Voss et al. |
| 7,004,955 B2 | 2/2006 | Shen |

(56) References Cited

U.S. PATENT DOCUMENTS

| | | |
|---|---|---|
| 7,004,956 B2 | 2/2006 | Palmer |
| 7,008,434 B2 | 3/2006 | Kurz et al. |
| 7,033,376 B2 | 4/2006 | Tsukernik |
| 7,041,116 B2 | 5/2006 | Goto |
| 7,048,758 B2 | 5/2006 | Boyle |
| 7,058,456 B2 | 6/2006 | Pierce |
| 7,063,707 B2 | 6/2006 | Bose |
| 7,153,320 B2 | 12/2006 | Euteneuer et al. |
| 7,175,655 B1 | 2/2007 | Malaei |
| 7,179,273 B1 | 2/2007 | Palmer et al. |
| 7,220,269 B1 | 5/2007 | Ansel |
| 7,220,271 B2 | 5/2007 | Clubb |
| 7,226,464 B2 | 6/2007 | Garner et al. |
| 7,229,472 B2 | 6/2007 | DePalma et al. |
| 7,232,462 B2 | 6/2007 | Schaeffer |
| 7,288,112 B2 | 10/2007 | Denardo et al. |
| 7,306,618 B2 | 12/2007 | Demond |
| 7,316,692 B2 | 1/2008 | Huffmaster |
| 7,323,001 B2 | 1/2008 | Cubb |
| 7,331,976 B2 | 2/2008 | McGuckin, Jr. et al. |
| 7,344,550 B2 | 3/2008 | Carrison et al. |
| 7,399,308 B2 | 7/2008 | Borillo et al. |
| 7,410,491 B2 | 8/2008 | Hopkins |
| 7,452,496 B2 | 11/2008 | Brady et al. |
| 7,491,215 B2 | 2/2009 | Vale et al. |
| 7,491,216 B2 | 2/2009 | Brady |
| 7,510,565 B2 | 3/2009 | Gilson et al. |
| 7,534,252 B2 | 5/2009 | Sepetka |
| 7,556,636 B2 | 7/2009 | Mazzocchi |
| 7,582,111 B2 | 9/2009 | Krolik et al. |
| 7,594,926 B2 | 9/2009 | Linder |
| 7,604,649 B2 | 10/2009 | McGuckin et al. |
| 7,618,434 B2 | 11/2009 | Santra et al. |
| 7,662,165 B2 | 2/2010 | Gilson et al. |
| 7,670,356 B2 | 3/2010 | Mazzocchi |
| 7,691,121 B2 | 4/2010 | Rosenbluth |
| 7,691,124 B2 | 4/2010 | Balgobin |
| 7,708,770 B2 | 5/2010 | Linder |
| 7,736,385 B2 | 6/2010 | Agnew |
| 7,766,934 B2 | 8/2010 | Pal |
| 7,771,452 B2 | 8/2010 | Pal |
| 7,780,694 B2 | 8/2010 | Palmer |
| 7,780,696 B2 | 8/2010 | Daniel et al. |
| 7,819,893 B2 | 10/2010 | Brady et al. |
| 7,828,815 B2 | 11/2010 | Mazzocchi |
| 7,846,176 B2 | 11/2010 | Mazzocchi |
| 7,846,175 B2 | 12/2010 | Bonnette et al. |
| 7,850,708 B2 | 12/2010 | Pal |
| 7,887,560 B2 | 2/2011 | Kusleika |
| 7,901,426 B2 | 3/2011 | Gilson et al. |
| 7,914,549 B2 | 3/2011 | Morsi |
| 7,922,732 B2 | 4/2011 | Mazzocchi |
| 7,927,784 B2 | 4/2011 | Simpson |
| 7,931,659 B2 | 4/2011 | Bose et al. |
| 7,998,165 B2 | 8/2011 | Huffmaster |
| 8,002,822 B2 | 8/2011 | Glocker et al. |
| 8,021,379 B2 | 9/2011 | Thompson et al. |
| 8,021,380 B2 | 9/2011 | Thompson et al. |
| 8,043,326 B2 | 10/2011 | Hancock et al. |
| 8,048,151 B2 | 11/2011 | O'Brien et al. |
| 8,052,640 B2 | 11/2011 | Fiorella et al. |
| 8,057,497 B1 | 11/2011 | Raju et al. |
| 8,066,757 B2 | 11/2011 | Ferrera et al. |
| 8,070,791 B2 | 12/2011 | Ferrera et al. |
| 8,088,140 B2 | 1/2012 | Ferrera et al. |
| 8,100,935 B2 | 1/2012 | Rosenbluth et al. |
| 8,109,941 B2 | 2/2012 | Richardson |
| 8,118,829 B2 | 2/2012 | Carrison et al. |
| 8,123,769 B2 | 2/2012 | Osborne |
| 8,137,377 B2 | 3/2012 | Palmer et al. |
| 8,142,422 B2 | 3/2012 | Makower et al. |
| 8,142,442 B2 | 3/2012 | Palmer et al. |
| 8,182,508 B2 | 5/2012 | Magnuson et al. |
| 8,187,298 B2 | 5/2012 | Pal |
| 8,246,641 B2 | 8/2012 | Osborne et al. |
| 8,246,672 B2 | 8/2012 | Osborne |
| 8,252,017 B2 | 8/2012 | Paul, Jr. et al. |
| 8,252,018 B2 | 8/2012 | Valaie |
| 8,357,178 B2 | 1/2013 | Grandfield et al. |
| 8,357,179 B2 | 1/2013 | Grandfield et al. |
| 8,357,893 B2 | 1/2013 | Xu et al. |
| 8,361,095 B2 | 1/2013 | Osborne |
| 8,366,663 B2 | 2/2013 | Fiorella et al. |
| 8,372,133 B2 | 2/2013 | Douk et al. |
| 8,409,215 B2 | 4/2013 | Sepetka et al. |
| 8,419,748 B2 | 4/2013 | Valaie |
| 8,460,312 B2 | 6/2013 | Bose et al. |
| 8,460,313 B2 | 6/2013 | Huffmaster |
| 8,486,104 B2 | 7/2013 | Samson et al. |
| 8,529,596 B2 | 9/2013 | Grandfield et al. |
| 8,574,262 B2 | 11/2013 | Ferrera et al. |
| 8,579,915 B2 | 11/2013 | French et al. |
| 8,585,713 B2 | 11/2013 | Ferrera et al. |
| 8,608,761 B2 | 12/2013 | Osbourne et al. |
| 8,679,142 B2 | 3/2014 | Slee et al. |
| 8,696,622 B2 | 4/2014 | Fiorella et al. |
| 8,702,652 B2 | 4/2014 | Fiorella et al. |
| 8,702,724 B2 | 4/2014 | Olsen et al. |
| 8,784,434 B2 | 7/2014 | Rosenbluth et al. |
| 8,784,441 B2 | 7/2014 | Rosenbluth et al. |
| 8,795,305 B2 | 8/2014 | Grandfield et al. |
| 8,795,317 B2 | 8/2014 | Grandfield et al. |
| 8,795,345 B2 | 8/2014 | Grandfield et al. |
| 8,814,892 B2 | 8/2014 | Galdonik et al. |
| 8,814,925 B2 | 8/2014 | Hilaire et al. |
| 8,900,265 B1 | 12/2014 | Ulm, III |
| 8,939,991 B2 | 1/2015 | Krolick et al. |
| 8,945,143 B2 | 2/2015 | Ferrera et al. |
| 8,945,172 B2 | 2/2015 | Ferrera et al. |
| 8,968,330 B2 | 3/2015 | Rosenbluth et al. |
| 9,039,749 B2 | 5/2015 | Shrivastava et al. |
| 9,072,537 B2 | 7/2015 | Grandfield et al. |
| 9,113,936 B2 | 8/2015 | Palmer et al. |
| 9,119,656 B2 | 9/2015 | Bose et al. |
| 9,138,307 B2 | 9/2015 | Valaie |
| 9,149,609 B2 | 10/2015 | Ansel et al. |
| 9,155,552 B2 | 10/2015 | Ulm, III |
| 9,161,766 B2 | 10/2015 | Slee et al. |
| 9,173,668 B2 | 11/2015 | Ulm, III |
| 9,186,487 B2 | 11/2015 | Dubrul et al. |
| 9,198,687 B2 | 12/2015 | Fulkerson et al. |
| 9,204,887 B2 | 12/2015 | Cully et al. |
| 9,221,132 B2 | 12/2015 | Bowman |
| 9,232,992 B2 | 1/2016 | Heidner |
| 9,532,792 B2 | 1/2017 | Galdonik et al. |
| 9,532,873 B2 | 1/2017 | Kelley |
| 9,533,344 B2 | 1/2017 | Monetti et al. |
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,125 B2 | 2/2017 | Bowman et al. |
| 9,572,982 B2 | 2/2017 | Burnes et al. |
| 9,579,484 B2 | 2/2017 | Barnell |
| 9,585,642 B2 | 3/2017 | Dinsmoor et al. |
| 9,615,832 B2 | 4/2017 | Bose et al. |
| 9,615,951 B2 | 4/2017 | Bennett et al. |
| 9,622,753 B2 | 4/2017 | Cox |
| 9,636,115 B2 | 5/2017 | Henry et al. |
| 9,636,439 B2 | 5/2017 | Chu et al. |
| 9,642,635 B2 | 5/2017 | Vale et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,989 B2 | 5/2017 | Cruise et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign et al. |

(56) References Cited

U.S. PATENT DOCUMENTS

| | | |
|---|---|---|
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,764,111 B2 | 9/2017 | Gulachenski |
| 9,770,251 B2 | 9/2017 | Bowman et al. |
| 9,770,577 B2 | 9/2017 | Li et al. |
| 9,775,621 B2 | 10/2017 | Tompkins et al. |
| 9,775,706 B2 | 10/2017 | Peterson et al. |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,980 B2 | 10/2017 | Karino et al. |
| 9,808,599 B2 | 11/2017 | Bowman et al. |
| 9,833,252 B2 | 12/2017 | Sepetka et al. |
| 9,833,604 B2 | 12/2017 | Lam et al. |
| 9,833,625 B2 | 12/2017 | Waldhauser et al. |
| 10,028,759 B2 | 7/2018 | Wallace et al. |
| 10,149,692 B2 | 12/2018 | Turjman et al. |
| 10,265,086 B2 | 4/2019 | Vale |
| 10,716,915 B2 | 7/2020 | Ogle et al. |
| 10,610,668 B2 | 8/2020 | Burkholz et al. |
| 2001/0001315 A1 | 5/2001 | Bates |
| 2001/0016755 A1 | 8/2001 | Addis |
| 2001/0041899 A1 | 11/2001 | Foster |
| 2001/0044598 A1 | 11/2001 | Parodi |
| 2001/0051810 A1 | 12/2001 | Dubrul |
| 2002/0002383 A1 | 1/2002 | Sepetka et al. |
| 2002/0016609 A1 | 2/2002 | Wensel |
| 2002/0022859 A1 | 2/2002 | Hogendijk |
| 2002/0026211 A1 | 2/2002 | Khosravi |
| 2002/0049468 A1 | 4/2002 | Streeter |
| 2002/0052620 A1 | 5/2002 | Barvut |
| 2002/0068954 A1 | 6/2002 | Foster |
| 2002/0072764 A1* | 6/2002 | Sepetka ............ A61M 25/0082 606/200 |
| 2002/0082558 A1 | 6/2002 | Samson |
| 2002/0091407 A1 | 7/2002 | Zadno-Azizi et al. |
| 2002/0095171 A1 | 7/2002 | Belef |
| 2002/0123765 A1 | 9/2002 | Sepetka |
| 2002/0143362 A1 | 10/2002 | Macoviak et al. |
| 2002/0156455 A1 | 10/2002 | Barbut |
| 2002/0161393 A1 | 10/2002 | Demond |
| 2002/0165576 A1 | 11/2002 | Boyle et al. |
| 2002/0173819 A1 | 11/2002 | Leeflang et al. |
| 2002/0177800 A1 | 11/2002 | Bagaoisan et al. |
| 2002/0188276 A1 | 12/2002 | Evans |
| 2003/0004536 A1 | 1/2003 | Boylan et al. |
| 2003/0004538 A1 | 1/2003 | Secrest |
| 2003/0004542 A1 | 1/2003 | Wensel |
| 2003/0009146 A1 | 1/2003 | Muni |
| 2003/0009191 A1 | 1/2003 | Wensel |
| 2003/0023204 A1 | 1/2003 | Vo et al. |
| 2003/0040769 A1 | 2/2003 | Kelley et al. |
| 2003/0040772 A1 | 2/2003 | Hyodoh et al. |
| 2003/0050663 A1 | 3/2003 | Khachin |
| 2003/0105484 A1 | 6/2003 | Boyle et al. |
| 2003/0125798 A1 | 7/2003 | Matrin |
| 2003/0130682 A1 | 7/2003 | Broome et al. |
| 2003/0144687 A1 | 7/2003 | Brady et al. |
| 2003/0153940 A1 | 8/2003 | Nohilly et al. |
| 2003/0153943 A1 | 8/2003 | Michael et al. |
| 2003/0153944 A1 | 8/2003 | Phung |
| 2003/0163064 A1 | 8/2003 | Vrba |
| 2003/0163158 A1 | 8/2003 | Wlite |
| 2003/0171769 A1 | 9/2003 | Barbut |
| 2003/0176884 A1 | 9/2003 | Berrada et al. |
| 2003/0195537 A1 | 10/2003 | Dubrul |
| 2003/0195554 A1 | 10/2003 | Shen |
| 2003/0199917 A1 | 10/2003 | Knudson |
| 2003/0204202 A1 | 10/2003 | Palmer |
| 2003/0212430 A1 | 11/2003 | Bose |
| 2003/0216611 A1 | 11/2003 | Vu |
| 2003/0236533 A1 | 12/2003 | Wilson |
| 2004/0010280 A1 | 1/2004 | Adams et al. |
| 2004/0010282 A1 | 1/2004 | Kusleika |
| 2004/0014002 A1 | 1/2004 | Lundgren |
| 2004/0068288 A1 | 4/2004 | Palmer et al. |
| 2004/0073243 A1 | 4/2004 | Sepetka |
| 2004/0079429 A1 | 4/2004 | Miller |
| 2004/0082962 A1* | 4/2004 | Demarais ......... A61M 25/0023 606/128 |
| 2004/0093065 A1 | 5/2004 | Yachia et al. |
| 2004/0133231 A1 | 7/2004 | Maitland |
| 2004/0138692 A1 | 7/2004 | Phung |
| 2004/0153118 A1 | 8/2004 | Clubb |
| 2004/0193107 A1 | 9/2004 | Pierpont et al. |
| 2004/0199202 A1 | 10/2004 | Dubrul et al. |
| 2004/0260333 A1 | 12/2004 | Dubrul et al. |
| 2005/0015047 A1 | 1/2005 | Shah |
| 2005/0020974 A1 | 1/2005 | Noriega |
| 2005/0033348 A1 | 2/2005 | Sepetka |
| 2005/0038447 A1 | 2/2005 | Huffmaster |
| 2005/0038468 A1 | 2/2005 | Panetta et al. |
| 2005/0049619 A1 | 3/2005 | Sepetka |
| 2005/0049669 A1 | 3/2005 | Jones |
| 2005/0049670 A1 | 3/2005 | Jones et al. |
| 2005/0055033 A1 | 3/2005 | Leslie et al. |
| 2005/0055047 A1 | 3/2005 | Greenhalgh |
| 2005/0059995 A1 | 3/2005 | Sepetka |
| 2005/0085849 A1 | 4/2005 | Sepetka |
| 2005/0090857 A1 | 4/2005 | Kusleika et al. |
| 2005/0125024 A1 | 6/2005 | Sepetka |
| 2005/0171566 A1 | 8/2005 | Kanamaru |
| 2005/0187570 A1 | 8/2005 | Nguyen et al. |
| 2005/0267491 A1 | 8/2005 | Kellett et al. |
| 2005/0216030 A1 | 9/2005 | Sepetka |
| 2005/0216050 A1 | 9/2005 | Sepetka |
| 2005/0288686 A1 | 9/2005 | Sepetka |
| 2005/0228417 A1 | 10/2005 | Teitelbaum et al. |
| 2006/0009785 A1* | 1/2006 | Maitland ............ A61B 17/221 606/113 |
| 2006/0009799 A1 | 1/2006 | Kleshinski et al. |
| 2006/0010636 A1 | 1/2006 | Vacher |
| 2006/0030933 A1 | 2/2006 | DeLeggge et al. |
| 2006/0058836 A1 | 3/2006 | Bose |
| 2006/0058837 A1 | 3/2006 | Bose |
| 2006/0058838 A1 | 3/2006 | Bose |
| 2006/0064151 A1 | 3/2006 | Guterman |
| 2006/0149313 A1 | 7/2006 | Arguello et al. |
| 2006/0155305 A1 | 7/2006 | Freudenthal |
| 2006/0155322 A1 | 7/2006 | Sater et al. |
| 2006/0161187 A1 | 7/2006 | Levine et al. |
| 2006/0195137 A1 | 8/2006 | Sepetka |
| 2006/0224177 A1 | 10/2006 | Finitsis |
| 2006/0224179 A1 | 10/2006 | Kucharczyk |
| 2006/0229638 A1 | 10/2006 | Abrams et al. |
| 2006/0282111 A1 | 12/2006 | Morsi |
| 2006/0287701 A1 | 12/2006 | Pal |
| 2007/0088383 A1 | 4/2007 | Pal et al. |
| 2007/0142858 A1 | 6/2007 | Bates |
| 2007/0149996 A1 | 6/2007 | Coughlin |
| 2007/0156170 A1 | 7/2007 | Hancock |
| 2007/0165170 A1 | 7/2007 | Fukuda |
| 2007/0191866 A1 | 8/2007 | Palmer et al. |
| 2007/0198028 A1 | 8/2007 | Miloslavski |
| 2007/0198051 A1 | 8/2007 | Clubb et al. |
| 2007/0198075 A1 | 8/2007 | Levy |
| 2007/0208367 A1 | 9/2007 | Fiorella |
| 2007/0208371 A1 | 9/2007 | French |
| 2007/0213765 A1 | 9/2007 | Adams et al. |
| 2007/0225749 A1 | 9/2007 | Martin |
| 2007/0239254 A1 | 10/2007 | Chia et al. |
| 2007/0244505 A1 | 10/2007 | Gilson et al. |
| 2007/0270902 A1 | 11/2007 | Slazas et al. |
| 2007/0288038 A1 | 12/2007 | Bimbo |
| 2008/0045881 A1 | 2/2008 | Teitelbaum et al. |

(56) References Cited

U.S. PATENT DOCUMENTS

| | | |
|---|---|---|
| 2008/0082107 A1 | 4/2008 | Miller et al. |
| 2008/0086190 A1 | 4/2008 | Ta |
| 2008/0091223 A1 | 4/2008 | Pokorney |
| 2008/0097398 A1 | 4/2008 | Mitelberg |
| 2008/0109031 A1 | 5/2008 | Sepetka |
| 2008/0109032 A1 | 5/2008 | Sepetka |
| 2008/0119886 A1 | 5/2008 | Greenhalgh et al. |
| 2008/0177296 A1 | 7/2008 | Sepetka |
| 2008/0183197 A1 | 7/2008 | Sepetka |
| 2008/0183198 A1 | 7/2008 | Sepetka |
| 2008/0183205 A1 | 7/2008 | Sepetka |
| 2008/0188876 A1 | 8/2008 | Sepetka |
| 2008/0188885 A1 | 8/2008 | Sepetka |
| 2008/0188928 A1 | 8/2008 | Salahieh |
| 2008/0200946 A1 | 8/2008 | Braun |
| 2008/0215077 A1 | 9/2008 | Sepetka |
| 2008/0221600 A1 | 9/2008 | Dieck et al. |
| 2008/0228209 A1 | 9/2008 | DeMello et al. |
| 2008/0234706 A1 | 9/2008 | Sepetka |
| 2008/0243170 A1 | 10/2008 | Jenson |
| 2008/0255596 A1 | 10/2008 | Jenson |
| 2008/0262528 A1 | 10/2008 | Martin |
| 2008/0262532 A1 | 10/2008 | Martin |
| 2008/0275488 A1 | 11/2008 | Fleming |
| 2008/0275493 A1 | 11/2008 | Farmiga |
| 2008/0281350 A1 | 11/2008 | Sepetka |
| 2008/0312681 A1 | 12/2008 | Ansel |
| 2009/0024157 A1 | 1/2009 | Anukhin |
| 2009/0054918 A1* | 2/2009 | Henson ............... A61B 17/221 606/159 |
| 2009/0069828 A1 | 3/2009 | Martin |
| 2009/0076539 A1 | 3/2009 | Valaie |
| 2009/0105722 A1 | 4/2009 | Fulkerson |
| 2009/0105737 A1 | 4/2009 | Fulkerson |
| 2009/0131908 A1 | 5/2009 | McKay |
| 2009/0163846 A1 | 5/2009 | Aklog et al. |
| 2009/0177206 A1 | 7/2009 | Lozier et al. |
| 2009/0182336 A1 | 7/2009 | Brenzel et al. |
| 2009/0221967 A1 | 9/2009 | Thommen et al. |
| 2009/0270815 A1 | 10/2009 | Stamp et al. |
| 2009/0281610 A1 | 11/2009 | Parker |
| 2009/0292297 A1 | 11/2009 | Ferrere |
| 2009/0292307 A1 | 11/2009 | Razack |
| 2009/0299374 A1 | 12/2009 | Tilson et al. |
| 2009/0299393 A1 | 12/2009 | Martin |
| 2009/0306702 A1 | 12/2009 | Miloslavski |
| 2010/0004607 A1 | 1/2010 | Wilson et al. |
| 2010/0030186 A1 | 2/2010 | Stivland |
| 2010/0030256 A1 | 2/2010 | Dubrul et al. |
| 2010/0087908 A1 | 4/2010 | Hilaire |
| 2010/0114017 A1* | 5/2010 | Lenker ............. A61B 17/12186 604/96.01 |
| 2010/0125326 A1 | 5/2010 | Kalstad |
| 2010/0125327 A1 | 5/2010 | Agnew |
| 2010/0191272 A1 | 7/2010 | Keating |
| 2010/0211094 A1 | 8/2010 | Sargent, Jr. |
| 2010/0249815 A1 | 9/2010 | Jantzen et al. |
| 2010/0268264 A1 | 10/2010 | Bonnett et al. |
| 2010/0268265 A1 | 10/2010 | Krolik et al. |
| 2010/0292726 A1 | 11/2010 | Olsen et al. |
| 2010/0305604 A1 | 12/2010 | Pah |
| 2010/0318178 A1 | 12/2010 | Rapaport et al. |
| 2010/0324649 A1 | 12/2010 | Mattsson |
| 2010/0331949 A1 | 12/2010 | Habib |
| 2011/0009875 A1 | 1/2011 | Grandfield et al. |
| 2011/0009940 A1 | 1/2011 | Grandfield et al. |
| 2011/0009942 A1 | 1/2011 | Gregorich |
| 2011/0022149 A1 | 1/2011 | Cox et al. |
| 2011/0054514 A1 | 3/2011 | Arcand |
| 2011/0054516 A1 | 3/2011 | Keegan |
| 2011/0060359 A1 | 3/2011 | Hannes |
| 2011/0077620 A1 | 3/2011 | deBeer |
| 2011/0098683 A1 | 4/2011 | Wiita et al. |
| 2011/0054504 A1 | 5/2011 | Wolf et al. |
| 2011/0125181 A1 | 5/2011 | Brady et al. |
| 2011/0130756 A1* | 6/2011 | Everson, Jr .... A61B 17/320725 606/41 |
| 2011/0152920 A1 | 6/2011 | Eckhouse et al. |
| 2011/0160763 A1 | 6/2011 | Ferrera et al. |
| 2011/0166586 A1 | 7/2011 | Sepetka et al. |
| 2011/0196414 A1 | 8/2011 | Porter et al. |
| 2011/0202088 A1 | 8/2011 | Eckhouse et al. |
| 2011/0213290 A1 | 9/2011 | Chin et al. |
| 2011/0213297 A1 | 9/2011 | Aklog et al. |
| 2011/0213393 A1 | 9/2011 | Aklog et al. |
| 2011/0213403 A1 | 9/2011 | Aboytes |
| 2011/0218564 A1 | 9/2011 | Drasler et al. |
| 2011/0224707 A1 | 9/2011 | Miloslavski et al. |
| 2011/0264132 A1 | 10/2011 | Strauss et al. |
| 2011/0276120 A1 | 11/2011 | Gilson et al. |
| 2011/0319917 A1 | 12/2011 | Ferrera et al. |
| 2012/0041449 A1 | 2/2012 | Eckhouse et al. |
| 2012/0041474 A1 | 2/2012 | Eckhouse et al. |
| 2012/0059356 A1 | 3/2012 | diPama et al. |
| 2012/0089216 A1 | 4/2012 | Rapaport et al. |
| 2012/0101510 A1 | 4/2012 | Lenker et al. |
| 2012/0116351 A1 | 5/2012 | Chomas et al. |
| 2012/0116440 A1 | 5/2012 | Leynov et al. |
| 2012/0143237 A1 | 6/2012 | Cam et al. |
| 2012/0143239 A1 | 6/2012 | Aklog et al. |
| 2012/0150147 A1 | 6/2012 | Leynov et al. |
| 2012/0165858 A1 | 6/2012 | Eckhouse et al. |
| 2012/0165859 A1 | 6/2012 | Eckhouse et al. |
| 2012/0215250 A1 | 8/2012 | Grandfield et al. |
| 2012/0277788 A1 | 11/2012 | Cattaneo |
| 2012/0283768 A1 | 11/2012 | Cox et al. |
| 2012/0296362 A1 | 11/2012 | Cam et al. |
| 2012/0316600 A1 | 12/2012 | Ferrera et al. |
| 2013/0030461 A1 | 1/2013 | Marks et al. |
| 2013/0046330 A1 | 2/2013 | McIntosh et al. |
| 2013/0046333 A1 | 2/2013 | Jones et al. |
| 2013/0046334 A1 | 2/2013 | Jones et al. |
| 2013/0116774 A1 | 5/2013 | Strauss et al. |
| 2013/0131614 A1 | 5/2013 | Hassan et al. |
| 2013/0144326 A1 | 6/2013 | Brady et al. |
| 2013/0144328 A1 | 6/2013 | Weber et al. |
| 2013/0158592 A1 | 6/2013 | Porter |
| 2013/0184703 A1 | 7/2013 | Shireman et al. |
| 2013/0184739 A1 | 7/2013 | Brady et al. |
| 2013/0197567 A1 | 8/2013 | Brady et al. |
| 2013/0226146 A1 | 8/2013 | Tekulve |
| 2013/0268050 A1 | 10/2013 | Wilson et al. |
| 2013/0281788 A1 | 10/2013 | Garrison |
| 2013/0325055 A1 | 12/2013 | Eckhouse et al. |
| 2013/0325056 A1 | 12/2013 | Eckhouse et al. |
| 2013/0345739 A1 | 12/2013 | Brady et al. |
| 2014/0046359 A1 | 2/2014 | Bowman et al. |
| 2014/0121672 A1 | 5/2014 | Folk |
| 2014/0128905 A1 | 5/2014 | Molaei |
| 2014/0135812 A1 | 5/2014 | Divino et al. |
| 2014/0180377 A1 | 6/2014 | Bose et al. |
| 2014/0188127 A1 | 7/2014 | Dubrul et al. |
| 2014/0194919 A1 | 7/2014 | Losardo et al. |
| 2014/0200607 A1 | 7/2014 | Sepetka et al. |
| 2014/0200608 A1 | 7/2014 | Brady et al. |
| 2014/0236220 A1 | 8/2014 | Inoue |
| 2014/0257362 A1 | 9/2014 | Eldenschink |
| 2014/0276922 A1 | 9/2014 | McLain et al. |
| 2014/0277053 A1 | 9/2014 | Wang et al. |
| 2014/0277079 A1 | 9/2014 | Vale et al. |
| 2014/0309657 A1 | 10/2014 | Ben-Ami |
| 2014/0309673 A1 | 10/2014 | Dacuycuy et al. |
| 2014/0330302 A1 | 11/2014 | Tekulve et al. |
| 2014/0343585 A1 | 11/2014 | Ferrera et al. |
| 2014/0364896 A1 | 12/2014 | Consigny |
| 2014/0371769 A1 | 12/2014 | Vale et al. |
| 2014/0371779 A1 | 12/2014 | Vale et al. |
| 2014/0371780 A1 | 12/2014 | Vale et al. |
| 2014/0379023 A1 | 12/2014 | Brady et al. |
| 2015/0018859 A1 | 1/2015 | Quick et al. |
| 2015/0018860 A1 | 1/2015 | Quick et al. |
| 2015/0080937 A1 | 3/2015 | Davidson |
| 2015/0081003 A1 | 3/2015 | Wainwright et al. |
| 2015/0112376 A1 | 4/2015 | Molaei et al. |

(56) References Cited

U.S. PATENT DOCUMENTS

| | | |
|---|---|---|
| 2015/0133990 A1 | 5/2015 | Davidson |
| 2015/0142043 A1 | 5/2015 | Furey |
| 2015/0164523 A1 | 6/2015 | Brady et al. |
| 2015/0238314 A1* | 8/2015 | Bortlein ............... A61F 2/2427 623/2.11 |
| 2015/0250497 A1 | 9/2015 | Marks et al. |
| 2015/0257775 A1 | 9/2015 | Gilvarry et al. |
| 2015/0297252 A1 | 10/2015 | Miloslavski et al. |
| 2015/0313617 A1 | 11/2015 | Grandfield et al. |
| 2015/0320431 A1 | 11/2015 | Ulm, III |
| 2015/0351770 A1 | 12/2015 | Fulton, III |
| 2015/0352325 A1 | 12/2015 | Quick |
| 2015/0359547 A1 | 12/2015 | Vale et al. |
| 2015/0374391 A1 | 12/2015 | Quick et al. |
| 2015/0374393 A1 | 12/2015 | Brady et al. |
| 2015/0374479 A1 | 12/2015 | Vale |
| 2016/0015402 A1 | 1/2016 | Brady et al. |
| 2016/0022296 A1 | 1/2016 | Brady et al. |
| 2016/0066921 A1 | 3/2016 | Brady et al. |
| 2016/0106448 A1 | 4/2016 | Brady et al. |
| 2016/0106449 A1 | 4/2016 | Brady et al. |
| 2016/0113663 A1 | 4/2016 | Brady et al. |
| 2016/0113664 A1 | 4/2016 | Brady et al. |
| 2016/0113665 A1 | 4/2016 | Brady et al. |
| 2016/0120558 A1 | 5/2016 | Brady et al. |
| 2016/0121080 A1 | 5/2016 | Cottone |
| 2016/0135829 A1* | 5/2016 | Holochwost ........... A61B 17/22 606/159 |
| 2016/0143653 A1 | 5/2016 | Vale et al. |
| 2016/0151079 A1 | 6/2016 | Aklog et al. |
| 2016/0192953 A1 | 7/2016 | Brady et al. |
| 2016/0192954 A1 | 7/2016 | Brady et al. |
| 2016/0192955 A1 | 7/2016 | Brady et al. |
| 2016/0192956 A1 | 7/2016 | Brady et al. |
| 2016/0228134 A1 | 8/2016 | Martin et al. |
| 2016/0256180 A1 | 9/2016 | Vale et al. |
| 2016/0262880 A1 | 9/2016 | Li et al. |
| 2016/0317168 A1 | 11/2016 | Brady et al. |
| 2017/0007264 A1 | 1/2017 | Cruise et al. |
| 2017/0007265 A1 | 1/2017 | Guo et al. |
| 2017/0020670 A1 | 1/2017 | Murray et al. |
| 2017/0020700 A1 | 1/2017 | Bienvenu et al. |
| 2017/0027640 A1 | 2/2017 | Kunis et al. |
| 2017/0027692 A1 | 2/2017 | Bonhoeffer |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0065401 A1 | 3/2017 | Fearnot et al. |
| 2017/0071614 A1 | 3/2017 | Vale et al. |
| 2017/0071737 A1 | 3/2017 | Kelley |
| 2017/0072452 A1 | 3/2017 | Monetti et al. |
| 2017/0079671 A1 | 3/2017 | Morero et al. |
| 2017/0079680 A1 | 3/2017 | Bowman |
| 2017/0079766 A1 | 3/2017 | Wang et al. |
| 2017/0079767 A1 | 3/2017 | Leon-Yip |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0086851 A1 | 3/2017 | Wallace et al. |
| 2017/0086862 A1 | 3/2017 | Vale et al. |
| 2017/0086863 A1 | 3/2017 | Brady et al. |
| 2017/0086996 A1 | 3/2017 | Peterson et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Granfield |
| 2017/0100183 A1 | 4/2017 | Iaizzo et al. |
| 2017/0105743 A1 | 4/2017 | Vale et al. |
| 2017/0112515 A1 | 4/2017 | Brady et al. |
| 2017/0113023 A1 | 4/2017 | Steingisser et al. |
| 2017/0147765 A1 | 5/2017 | Mehta |
| 2017/0151032 A1 | 6/2017 | Loisel |
| 2017/0165062 A1 | 6/2017 | Rothstein |
| 2017/0165065 A1 | 6/2017 | Rothstein et al. |
| 2017/0165454 A1 | 6/2017 | Tuohy et al. |
| 2017/0172554 A1 | 6/2017 | Bortlein et al. |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0252064 A1 | 9/2017 | Staunton |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder et al. |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |
| 2018/0042623 A1 | 2/2018 | Batiste |
| 2018/0193591 A1 | 7/2018 | Jaroch et al. |
| 2018/0235743 A1 | 8/2018 | Farago et al. |
| 2019/0021759 A1 | 1/2019 | Krolik et al. |
| 2019/0046219 A1 | 2/2019 | Marchand et al. |
| 2019/0192175 A1 | 6/2019 | Chida et al. |
| 2019/0209206 A1 | 7/2019 | Patel et al. |
| 2019/0216476 A1 | 7/2019 | Barry et al. |
| 2019/0255290 A1 | 8/2019 | Snyder et al. |
| 2019/0365411 A1 | 12/2019 | Avneri et al. |

FOREIGN PATENT DOCUMENTS

| | | |
|---|---|---|
| CN | 104507380 A | 4/2015 |
| CN | 104905873 A | 9/2015 |
| CN | 105307582 A | 2/2016 |
| CN | 105726163 A | 7/2016 |
| CN | 106232059 A | 12/2016 |
| DE | 20 2009 001 951 U1 | 4/2010 |
| DE | 10 2009 056 450 A1 | 6/2011 |
| DE | 10 2010 010 849 A1 | 9/2011 |
| DE | 10 2010 014 778 A1 | 10/2011 |
| DE | 10 2010 024 085 A1 | 12/2011 |
| DE | 10 2011 014 586 B3 | 9/2012 |
| EP | 2301450 A1 | 3/2011 |
| EP | 2628455 A1 | 8/2013 |
| EP | 3302312 A1 | 4/2018 |
| GB | 2498349 A | 7/2013 |
| JP | 9-19438 A | 1/1997 |
| WO | WO 93/04722 A2 | 3/1993 |
| WO | 94/24926 A1 | 11/1994 |
| WO | 97/27808 A1 | 8/1997 |
| WO | 97/38631 A1 | 10/1997 |
| WO | 99/20335 A1 | 4/1999 |

(56) References Cited

FOREIGN PATENT DOCUMENTS

| | | | |
|---|---|---|---|
| WO | 99/56801 | A2 | 11/1999 |
| WO | 99/60933 | A1 | 12/1999 |
| WO | 01/21077 | A1 | 3/2001 |
| WO | 02/02162 | A2 | 1/2002 |
| WO | 02/11627 | A2 | 2/2002 |
| WO | 02/43616 | A2 | 6/2002 |
| WO | 02/070061 | A1 | 9/2002 |
| WO | 02/094111 | A2 | 11/2002 |
| WO | 03/002006 | A1 | 1/2003 |
| WO | 03/018085 | A2 | 3/2003 |
| WO | 03/030751 | A1 | 4/2003 |
| WO | 03/051448 | A2 | 6/2003 |
| WO | 2004/028571 | A1 | 4/2004 |
| WO | 2004/056275 | A1 | 7/2004 |
| WO | 2005/000130 | A1 | 1/2005 |
| WO | 2005/027751 | A1 | 3/2005 |
| WO | 2005/027779 | A2 | 3/2005 |
| WO | 2006/021407 | A2 | 3/2006 |
| WO | 2006/031410 | A2 | 3/2006 |
| WO | 2006/107641 | A2 | 10/2006 |
| WO | 2006/135823 | A2 | 12/2006 |
| WO | 2007/054307 | A2 | 5/2007 |
| WO | 2007/068424 | A2 | 6/2007 |
| WO | 2008/034615 | A2 | 3/2008 |
| WO | 2008/051431 | A1 | 5/2008 |
| WO | 2008/131116 | A1 | 10/2008 |
| WO | 2009/019664 | A1 | 2/2009 |
| WO | 2009/031338 | A1 | 3/2009 |
| WO | 2009/076482 | A1 | 6/2009 |
| WO | 2009/086482 | A2 | 7/2009 |
| WO | 2009/105710 | A1 | 8/2009 |
| WO | WO 2009/103125 | A1 | 8/2009 |
| WO | 2010/010545 | A1 | 1/2010 |
| WO | 2010/046897 | A1 | 4/2010 |
| WO | 2010/075565 | A1 | 7/2010 |
| WO | 2010/102307 | A1 | 9/2010 |
| WO | 2010/146581 | A1 | 12/2010 |
| WO | 2011/013556 | A1 | 2/2011 |
| WO | 2011/066961 | A1 | 6/2011 |
| WO | 2011/082319 | A1 | 7/2011 |
| WO | 2011/095352 | A1 | 8/2011 |
| WO | 2011/106426 | A1 | 9/2011 |
| WO | 2011/110316 | A1 | 9/2011 |
| WO | 2012/052982 | A1 | 4/2012 |
| WO | 2012/064726 | A1 | 5/2012 |
| WO | 2012/081020 | A1 | 6/2012 |
| WO | 2012/110619 | A1 | 8/2012 |
| WO | 2012/120490 | A2 | 9/2012 |
| WO | 2012/156924 | A1 | 11/2012 |
| WO | 2013/016435 | A1 | 1/2013 |
| WO | 2013/072777 | A2 | 5/2013 |
| WO | 2013/105099 | A2 | 7/2013 |
| WO | 2013/109756 | A2 | 7/2013 |
| WO | 2014/081892 | A1 | 5/2014 |
| WO | 2014/139845 | A1 | 9/2014 |
| WO | 2014/169266 | A1 | 10/2014 |
| WO | 2014/178198 | A1 | 11/2014 |
| WO | 2015/061365 | A1 | 4/2015 |
| WO | 2015/134625 | A1 | 9/2015 |
| WO | 2015/179324 | A2 | 11/2015 |
| WO | WO 2015/179377 | A1 | 11/2015 |
| WO | 2015/189354 | A1 | 12/2015 |
| WO | 2016/010995 | A1 | 1/2016 |
| WO | WO 2017/004234 | A1 | 1/2017 |
| WO | 2018/193603 | A1 | 10/2018 |
| WO | WO 2018/178979 | A1 | 10/2018 |
| WO | WO 2019/064306 | A1 | 4/2019 |
| WO | WO 2019/079296 | A1 | 4/2019 |
| WO | WO 2020/139979 | A1 | 7/2020 |

OTHER PUBLICATIONS

Extended European Search Report dated Jul. 28, 2021 issued in European Patent Application No. 20 21 0069.
Extended European Search Report dated Aug. 5, 2021 issued in European Patent Application No. 21 16 7037.

* cited by examiner

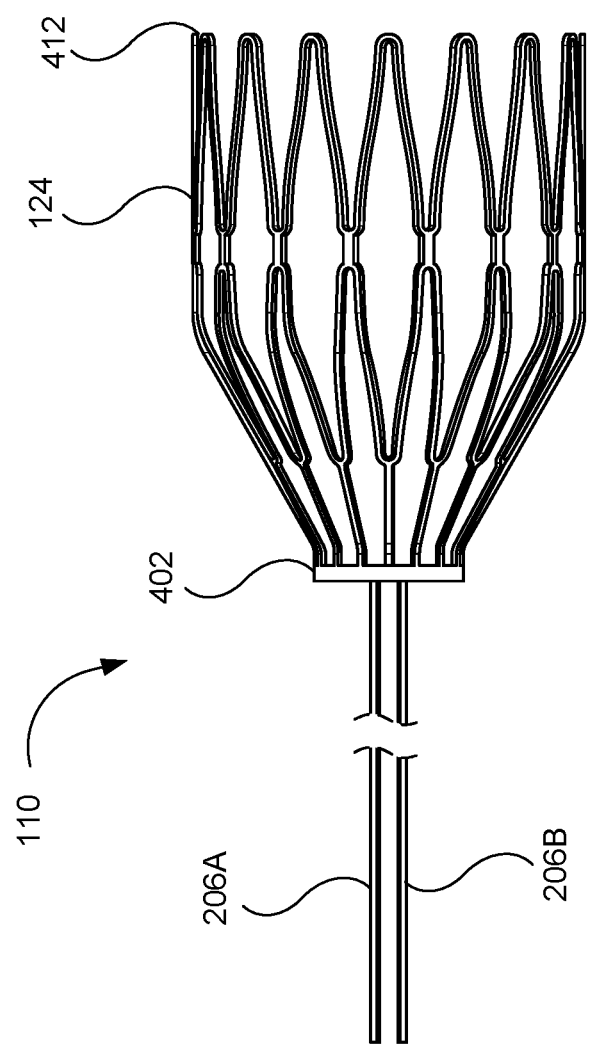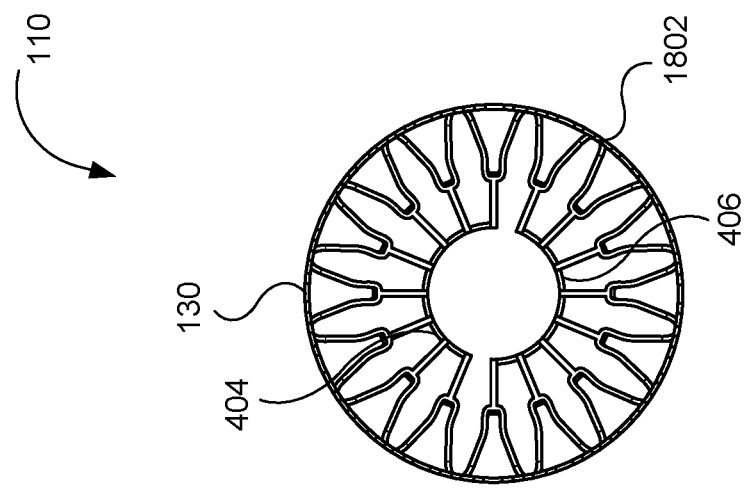
FIG. 18A
FIG. 18B

ACTUATED CLOT RETRIEVAL CATHETER

CROSS REFERENCE TO RELATED APPLICATIONS

This application claims priority, and benefit under 35 U.S.C. § 119(e), to U.S. Provisional Patent Application No. 62/813,723, filed 4 Mar. 2019, which is incorporated herein by reference as if fully set forth below.

FIELD OF THE DISCLOSURE

The present disclosure generally relates to devices and methods for removing acute blockages from blood vessels during intravascular medical treatments. More specifically, the present disclosure relates to an actuated clot retrieval catheter.

BACKGROUND

Clot retrieval catheters and devices are used in mechanical thrombectomy for endovascular intervention, often in cases where patients are suffering from conditions such as acute ischemic stroke (AIS), myocardial infarction (MI), and pulmonary embolism (PE). Accessing remote areas such as the neurovascular bed is challenging with conventional technology, as the target vessels are small in diameter, distant relative to the site of insertion, and are highly tortuous.

The clot itself can complicate procedures by taking on a number of complex morphologies and consistencies, ranging from simple tube-shaped structures which assume the shape of the vessel to long, strand-like arrangements that can span multiple vessels at one time. The age of a clot can also affect its compliance, with older clots tending to be less compressible than fresh clots. Fibrin rich clots also present a challenge in having a sticky nature that can cause a clot to roll along the outer surface of a mechanical thrombectomy device rather than being gripped effectively. Combinations of soft and firm clot regions can also separate during aspiration, with fragmentation leading to distal embolization which can occur in vessels that cannot be reached with currently available devices. Additionally, breaking the bonds adhering the clot to the vessel wall without damaging fragile vessels is a significant challenge.

Conventional clot retrieval catheters, especially those for operating in the neurovascular blood vessels, can suffer from a number of drawbacks. First, the diameters of the catheters themselves must be small enough to be advanced into the vasculature, which is very small in the context of the neurovascular system. The catheter must also be sufficiently flexible to navigate the vasculature and endure high strains, while also having the axial stiffness to offer smooth advancement along the route. Once at the target site, typical objects to be retrieved from the body can be substantially larger in size than the catheter tip, making it more difficult to retrieve objects into the tip. For example, fibrin-rich clots can often be difficult to extract as they can become lodged in the tip of traditional fixed-mouth catheters. This lodging can cause softer portions of the clot to shear away from the firmer regions, leading to distal embolization.

Small diameters and fixed tip sizes can also be less efficient at directing the aspiration necessary to remove blood and thrombus material during the procedure. The aspiration suction must be strong enough such that any fragmentation occurring through the use of a mechanical thrombectomy device or other methods can, at the very least, be held stationary so that fragments cannot migrate and occlude distal vessels. When aspirating with a traditional fixed-mouth catheter, however, a significant portion of the aspiration flow ends up coming from vessel fluid proximal to the tip of the catheter where there is no clot. This significantly reduces aspiration efficiency, lowering the success rate of clot removal.

The disclosed design is aimed at providing an improved aspirating retrieval catheter which addresses the above-stated deficiencies.

SUMMARY

Examples presented herein include devices and methods for removing acute blockages from blood vessels during intravascular medical treatments. More specifically, the present disclosure relates to an actuated clot retrieval catheter system. An example system for retrieving an obstruction in a blood vessel can include a catheter, a first conductive wire, and an electronic circuit. The electronic circuit can provide a first current to the first conductive wire. A frame can be located near the distal end of the catheter and can be in electrical communication with the first conductive wire. The frame can include a shape memory material that enables the frame, or a portion thereof, to transition from a martensite phase to an austenite phase when heated to above the material's austenite finish temperature. At least a first portion of the frame can be expandable from a collapsed configuration to an expanded configuration upon being heated by the first current.

The shape memory material can have a transition temperature above approximately 37° C. In some examples, the shape memory material can have a transition temperature of from approximately 45° C. to 55° C.

The system can include a thermoelectric cooling circuit in electrical communication with the frame. The at least a first portion of the frame can be collapsible from the expanded configuration to the collapsed configuration upon removal of heat by the thermoelectric cooling circuit.

At least a second portion of the frame can be collapsible from an open configuration to a collapsed configuration upon being heated.

The system can include a second conductive wire in electrical communication with the second portion of the frame. The second conductive wire can receive a second current from the electronic circuit.

The system can include a membrane cover disposed around the frame.

The frame can be located within an inner lumen of the catheter. In other examples, the frame extends from the distal end, for example like a funnel, to capture the occlusion.

The system can include a thermocouple in electrical communication with the frame. The thermocouple can help to remove heat from at least a portion of the frame.

The shape memory material can be in a martensite phase when the at least a first portion of the frame is in the collapsed configuration. The shape memory material can be in an austenite phase when the at least a first portion of the frame is in the expanded configuration.

An example method of retrieving an occlusive thrombus from a blood vessel of a patient can include delivering a catheter comprising a frame to a target site. The frame can include a shape memory material. The method can include delivering a first current to the frame. The current running through the frame can heat the frame to cause at least a first portion of the frame to change from a collapsed configuration to an expanded configuration. The method can include aspirating the occlusive thrombus into the frame. The catheter can be withdrawn with the occlusive thrombus from the patient.

The shape memory material of the frame can have a transition temperature of from approximately 45° C. to 55° C.

The method can include deactivating the first current. By deactivating the first current, the at least a first portion of the frame can cool to cause the at least a first portion of the frame to collapse upon the occlusive thrombus.

The method can include cooling the at least a first portion of the frame with a thermoelectric cooling circuit to cause the at least a first portion of the frame to collapse upon the occlusive thrombus. The thermoelectric cooling circuit can include a Peltier chip, a thermoelectric wire, and the like.

The method can include delivering a second current to at least a second portion of the frame. The second current can create heat, through the resistance of the shape memory material, that causes the at least a second portion of the frame to change from an expanded configuration to a collapsed configuration and upon the occlusive thrombus.

The method can include monitoring a temperature of the frame with a thermocouple in communication with the frame. The method can include deactivating the first current when the temperature is above a first temperature. This can ensure the vessel is not damaged by excessive heat.

The frame can be located within an inner lumen of the catheter. In these examples, causing the at least a first portion of the frame to expand from a collapsed configuration to an expanded configuration can cause an inner diameter of the of the catheter to increase.

An example method of manufacturing an actuated clot retrieval system can include heat setting a first shape memory material into a first frame having an expanded configuration. The method can include allowing the first shape memory material to cool and the first frame to collapse into a collapsed configuration. The method can include connecting the first frame to a first end of a first conductive wire disposed within a catheter wall of a catheter. The method can include connecting a second end of the first conductive wire to an electronic circuit. The method can include applying a membrane to the first frame and to a distal end of the catheter.

The method can include heat setting a second shape memory material into a second frame having a collapsed configuration. The method can include connecting the second frame to a first end of a second conductive wire disposed within the catheter wall. The method can include connecting a second end of the second conductive wire to the electronic circuit. The method can include applying the membrane to the second frame.

The first shape memory material and the second shape memory material can different alloys, and the first frame and the second frame can be coaxial and connected to the distal end of the catheter. In other words, the second frame can be circumferentially positioned upon the second frame such that the second frame can close upon the first frame.

The first shape memory material and the second shape memory material can include the same alloy, and the first shape memory material and the second shape memory material can have different austenite finish temperatures.

The method can include providing a first catheter layer and disposing the first conductive wire on the first catheter layer. The method can include applying a second catheter layer over the first conductive wire and a first anchor strut of the first frame. Connecting the first frame to the first end of the first conductive wire can include connecting the first anchor strut to the first conductive wire prior to applying the second catheter layer.

The method can include encasing the first frame with a ring to hold the first frame in the collapsed configuration. Applying the membrane to the first frame can include dipping the first frame and the ring into a membrane material and allowing the membrane material to cool.

BRIEF DESCRIPTION OF THE DRAWINGS

The above and further aspects of this disclosure are further discussed with the following description of the accompanying drawings, in which like numerals indicate like structural elements and features in various figures. The drawings are not necessarily to scale, emphasis instead being placed upon illustrating principles of the disclosure. The figures depict one or more implementations of the inventive devices, by way of example only, not by way of limitation. It is expected that those of skill in the art can conceive of and combining elements from multiple figures to better suit the needs of the user.

FIGS. 16-18B depict example designs for a frame, according to aspects of the present disclosure;

DETAILED DESCRIPTION

Figure 1A:
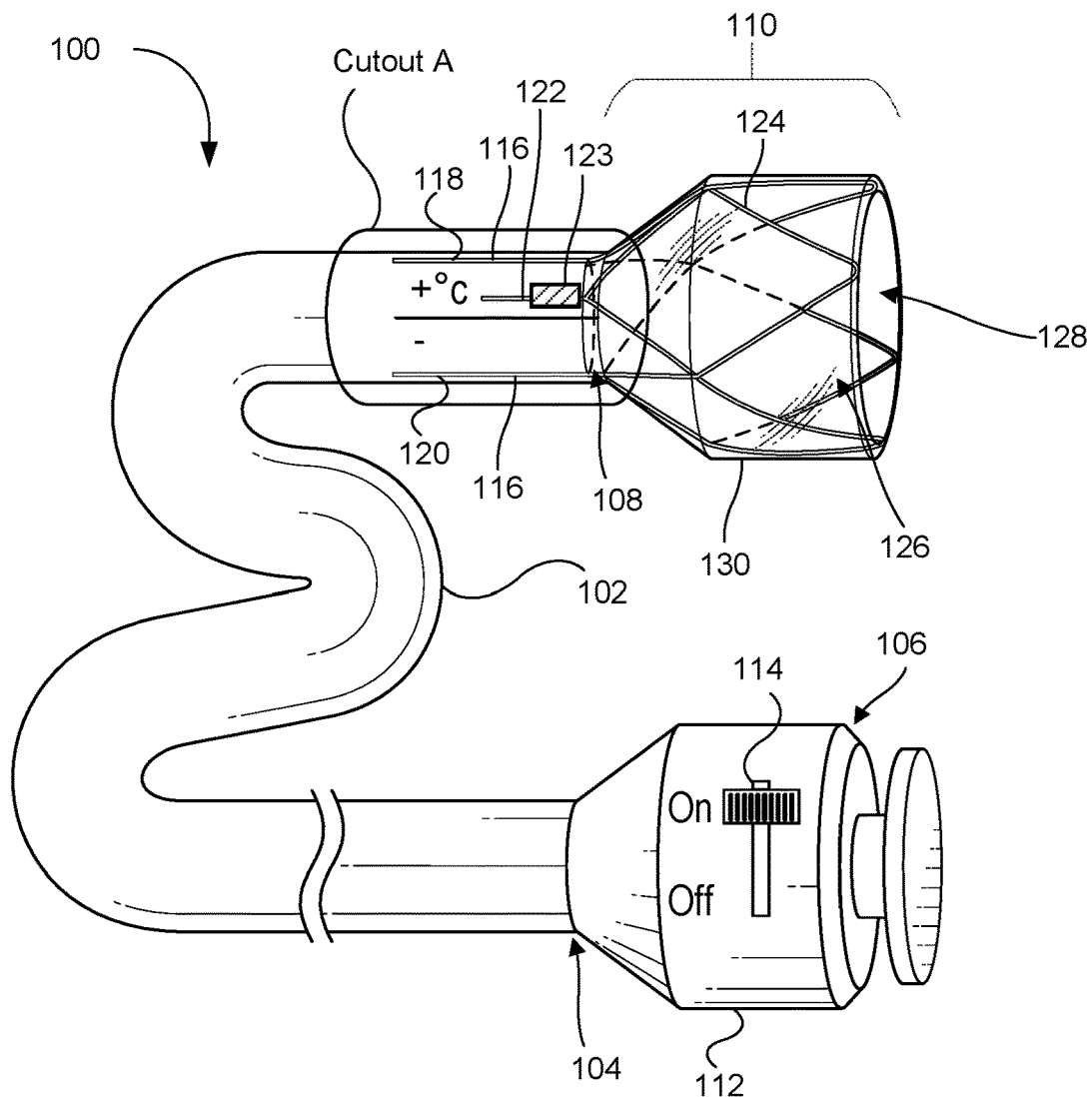
FIGS. 1A and 1B are side-view illustrations of an exemplary actuated clot retrieval system, according to aspects of the present disclosure.

The herein disclosed solution is directed to a clot retrieval catheter capable of providing local flow restriction/arrest via a modular distal frame. Flow restriction and large tipped designs offer substantially greater aspiration efficiency. Such advantages can also be especially beneficial in the case of stroke intervention procedures, where vessels in the neurovascular bed are particularly small and circuitous, and as a result a tailored axial and bending stiffness profile can inhibit kinking and binding. The catheter can also be compatible with relatively low-profile access sheaths and outer catheters, so that a puncture wound in the patient's groin (in the case of femoral access) can be easily and reliably closed. The catheter can also feature internal and/or external low-friction liners, and an outer polymer jacket or membrane disposed around the support structure. The membrane can be an elastomeric material that encapsulates the frame or is fitted over the frame so that the frame can move independently of the membrane. The membrane can be tight or loose fitting. A loose-fitting elastomeric membrane will be easier to open that a tight fitting membrane. The membrane can be baggy and made of a non-elastomeric material such that the force to open the membrane is low compared to that of a tight-fitting elastomeric membrane. The membrane can be inverted to extend distally from a proximal location radially inwardly of the frame before reverting back to extend proximally radially outwardly of the frame and wherein the inner and outer layers of the membrane are bonded or reflowed together at a proximal location or for the full length of the membrane. The membrane can comprise an inner and an outer tube, the proximal and distal ends of the inner and outer tube being bonded together or reflowed such that the two tubes form a sock around the frame, the frame being free to move/expand within the sock.

These improvements can lead to safe and more rapid access of a catheter and other devices to complex areas in order to remove occlusions and shorten procedure times. While the description is in many cases in the context of mechanical thrombectomy treatments, the systems and methods can be adapted for other procedures and in other body passageways as well.

Accessing the various vessels within the vascular system, whether they are coronary, pulmonary, or cerebral, involves well-known procedural steps and the use of a number of conventional, commercially-available accessory products. These products, such as angiographic materials, rotating hemostasis valves, and guidewires are widely used in laboratory and medical procedures. When these products are employed in conjunction with the system and methods in the description below, their function and exact constitution are not known in the related art.

The present systems and methods employ the characteristics of shape memory materials to customize the distal dimensions of a clot-retrieval device. Shape memory materials are those materials, such as alloys, that can be deformed when cold and then expand to a predetermined shape when heated. Once the heat is removed from the material, the material can return to it's collapsed, pliable shape. This can be achieved by heating the shape memory material beyond an austenite finish (AF) temperature. Below the AF temperature, the shape material exits its martensite phase, which is characterized by high elasticity, pliability, and flexibility. Above the AF temperature, the shape material exists in its austenite phase, which is characterized by a more rigid state. The shape memory material can be heat set to a predetermined shape above its AF temperature such that, when the material is reheated to the AF temperature, the material returns to that predetermined shape.

Various embodiments described herein can include frames that can resemble a funnel sheath that, once expanded, can exert a radial force on the vasculature. Fluid can be aspirated into the expanded funnel and then into a catheter to capture a thrombus within the funnel. The frame can include a membrane covering that directs the aspirate into the catheter. In other examples, the frame can be disposed within an inner lumen of the catheter. As the frame expands and collapses, the inner diameter of the catheter can be increased and decreased to adjust the flow rate into the catheter.

The present disclosure provides a mechanism for heating the frame to its AF temperature to cause the frame to transition into its austenite phase. One or more conductive lead wires can provide a current to the frame. The natural electrical resistance of the shape memory material can then cause the frame to heat above the AF temperature. A thermocouple can also be provided to monitor the temperature of the frame such that the frame does not overheat and cause trauma to the surrounding vasculature. In some examples, a thermoelectric cooling circuit, such as a Peltier chip, can be provided to transition the frame back into its martensite phase. The present disclosure provides various example designs for frames.

Figure 1B:
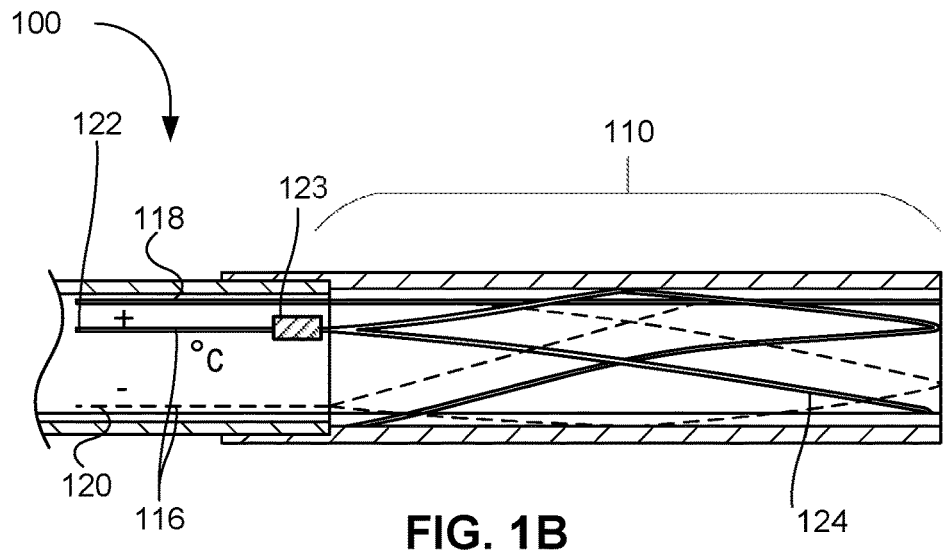

Various devices and methods are disclosed for providing an actuated clot retrieval catheter, and examples of the devices and methods will now be described with reference to the accompanying figures. FIGS. 1A and 1B provide an illustration of an example clot retrieval system 100. The system 100 can include a catheter 102 having a proximal end 104 proximal to a circuit housing 106 and a distal end 108. The catheter 102 can have a sufficiently small outer diameter to advance the catheter 102 through an outer catheter, such as an access sheath. The system 100 can include a frame 110 proximate the distal end 108 of the catheter 102. The frame 110 can extend beyond the distal end 108 of the catheter, as shown in FIGS. 1A and 1B. In some examples, the frame 110 can be disposed within an inner lumen of the catheter 102, as will be described in greater detail below. In another example, the frame 110 can be located along the length of the catheter 102 such the frame 110 can act as a closed "balloon," as will be described below with reference to FIG. 6.

The frame 110 can be encapsulated within an inverted membrane, dual layer sealed membrane or an overmoulded or dipped membrane. Where the frame 110 is housed within an inner and outer membrane layer, the frame can have unhindered movement. Where an overmoulded membrane is supplied, there may be more resistance as the frame 110 may be required to stretch more discrete areas of membrane material. It is appreciated that, as an electrical current will be passed through the frame 110, it can be insulated in order to contain the electrical current. The membrane material can serve to insulate the frame 110. The frame 110, acting as a resistor, can thereby generate heat under a current load.

The frame 110 can have an expanded configuration and a collapsed configuration. FIG. 1A shows a frame 110 in the shape of a funnel in an expanded configuration, while FIG. 1B shows the same frame 110 in a collapsed configuration. The frame 110 can include a shape memory material that enables the frame 110 to transition from a collapsed configuration to an expanded configuration, or vice versa, upon being heated and return to its previous configuration upon cooling. The shape memory material of the frame 110 can include alloys that have shape memory effect such that the material can transition from a martensite phase to an austenite phase. These materials can include, but are not limited to, a Ni—Ti (Nitinol) alloy, a Ni—Al alloy, an In—Ti alloy, an Ag—Cd alloy, an Au—Cd alloy, a Cu—Al—Ni alloy, a Cu—Sn alloy, a Cu—Zn alloy, a Mn—Cu alloy, and similar alloys.

Shape memory materials enable devices to be manufactured such that, once heated above an AF temperature, the device can be pre-set into a predetermined shape. Considering the example funnel-shaped frame 110 of FIGS. 1A and 1B, the frame 110 can be provided in a collapsed configuration (FIG. 1B). The frame 110 can then be heated to above the AF temperature of the shape memory material and then shaped into its final configuration (FIG. 1A). At this stage, the frame 110 is in its austenite phase. Once the frame 110 is re-cooled to below the AF temperature of the material, the frame 110 can return to its un-set shape. At this stage, the frame 110 is in its martensite phase Due to the low heat capacity of the frame 110, cooling can be achieved easily through conduction with the wires and/or thermocouple wires, and subsequentially through the catheter 102 jacket materials and/or membrane material.

Figure 1C:
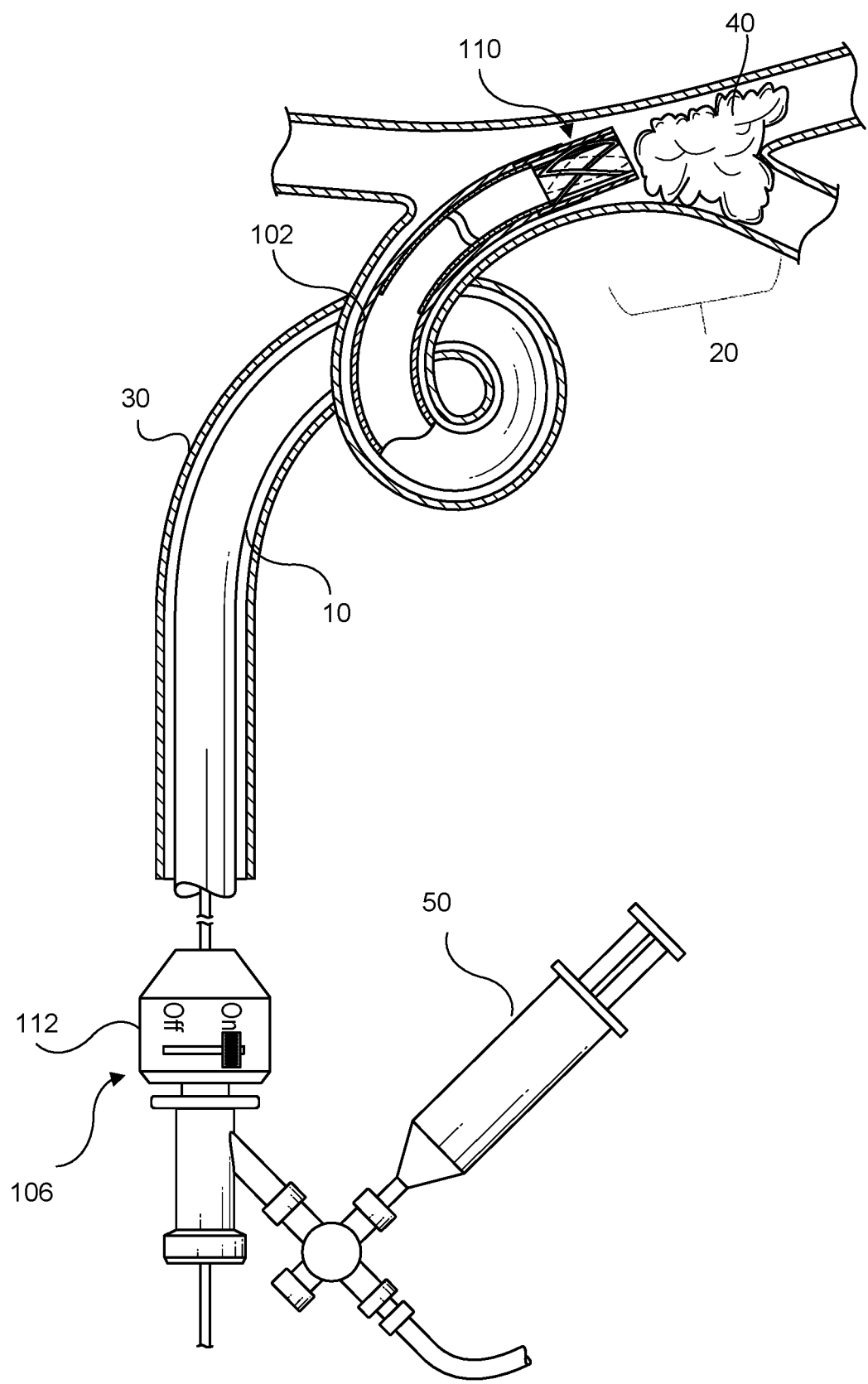
FIGS. 1C and 1D illustrate a method of delivering an exemplary actuated clot retrieval system to a target site within a vessel, according to aspects of the present disclosure.
Figure 1D:
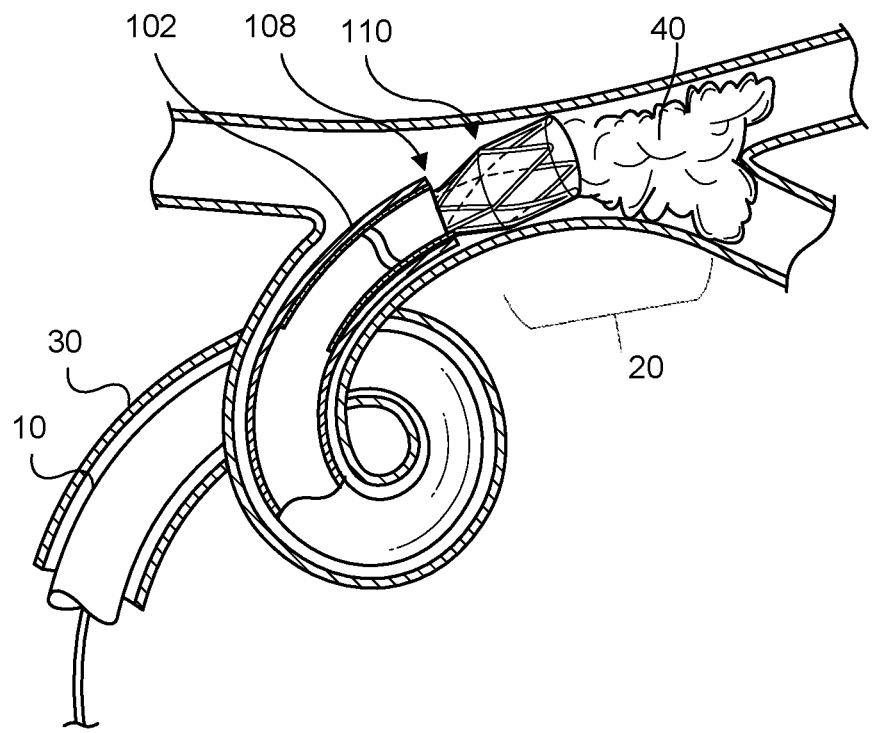

FIGS. 1C and 1D provide an example method of using the transition characteristics of shape memory materials to actuate a clot retrieval system 100. The actuated clot retrieval system 100 including the catheter 102 and frame 110 can be advanced to a target site 20 in a vessel 30 containing a clot 40. This can be completed by advancing the system 100 through an outer catheter 10, as shown in the figure. However, as will be described below, the catheter 102 and frame 110 can be advanced to the target site 10 without the need for an outer catheter 10. Once the catheter 102 and frame 110 reach the target site 20, the frame 110 can be in its martensite phase, characterized by high elasticity, pliability, and flexibility of the material. This can enable the frame 110 to advance through the winding vessel 30 with ease. Once the frame 110 is at the target site 20, the frame 110 can be heated, which is described in greater detail below, to enable the frame 110 to transition from martensite phase to austenite phase. In the examples shown in FIG. 1D, the frame 110 was heat set into a funnel sheath in its austenite phase such that, when heated, the frame 110 expands to a funnel to exert a force on the vessel 30. The clot 40 can then be aspirated into the frame 110 and removed from the target site 20. In some examples, the frame 110 can be actively cooled such that the frame 110 collapses into its martensite phase to capture the clot 40. Alternatively, the frame 110 can automatically cool due to the low heat capacity of the frame 110.

Referring again to FIGS. 1A and 1B, various shape memory materials, including the alloys described above, have different AF temperatures, enabling the system 100 to be customized for the particular procedure. Further, materials processed with a certain AF temperature can be reprocessed through subsequent processes involving heat treatment in order to reset the AF temperature to the desired range. The shape memory material can be selected or processed such that the AF temperature is above human blood (e.g., above 37° C.) so that the frame 110 is not inadvertently activated prior to reaching the intended activation location in a vessel. The AF temperature can be between 35° C. and 200° C. (e.g., between 37° C. and 65° C., between 40° C. and 60° C., etc.). Ideally the AF temperature can be in the range of 45 to 55° C. This can help ensure martensite properties for a highly flexible delivery configuration while minimizing the energy required to heat the frame 110 for expansion and rigid properties.

As used herein, the terms "about" or "approximately" for any numerical values or ranges indicate a suitable dimensional tolerance that allows the part or collection of components to function for its intended purpose. More specifically, "about" or "approximately" may refer to the range of values ±10% of the recited value, e.g. "about 50° C." may refer to the range of values from 45.001° C. to 54.999° C.

The frame 110 can be heated by providing a current to the frame 110. The high electrical resistance of the shape memory material, for example Nitinol, can cause the frame 110 to heat in response to the electrical current and the heat in turn cause the transition from the martensite to austenite phase. The system 100 can include an electronic circuit 112 to provide the required current to the frame 110. The electronic circuit 112 can be disposed within a circuit housing 106. The electronic circuit 112 can be activated with a switch 114. The electronic circuit 112 can feed from approximately 300 mA to approximately 1500 mA (e.g., approximately 500 mA to approximately 1000 mA) to the frame 110 using a power supply ranging, for example, from approximately 3 to 12V, more preferably from approximately 5 to 9V. The current can be pulsed from 1 to 1000 msec, more preferable from 100 to 500 msec with a break in current of between 1 and 1000 msec, more preferably from 1 to 100 msec. Pulsing allows the temperature of the frame to be maintained between a set temperature range, the on segment of the pulses heating and the off segment of the pulse allowing the frame to cool such that the temperature is kept between a range. The temperature can be monitored by a thermocouple such that the pulses can be altered if the temperature goes out of range; for example, a continuous feed of current can be used to ramp up the temperature quickly and the pulses can be lowered keep the temperature of the frame under the upper range.

One or more conductive wires 116 (e.g., a positive lead 118 and a negative lead 120) can extend between the electronic circuit 112 and the frame 110 to provide the electrical current to heat the frame 110. Cutout A of FIG. 1A shows the positive lead 118 and negative lead 120 attaching to the frame 110. The conductive wire 116 can be embedded within layers of the catheter 102 so that the wire is not exposed on the outer or inner surface of the catheter 102. This can enable the system 100 to be advanced into an outer catheter without the wire restricting the movement of the catheter 102 through the outer catheter. The conductive wires 116 can comprise copper or any other material suitable to provide a current to the frame 110.

The system 100 can include a thermocouple 122 connected to the frame 110 to monitor the temperature of the frame 110. If the frame 110 is heated above a certain temperature, the frame 110 can burn the surrounding vasculature. To this end, the thermocouple 122 can monitor the temperature of the frame 110 as it is heated by the current. If the frame 110 exceeds a certain temperature, for example 50° C., the thermocouple 122 can communicate this information to the electronic circuit 112 to deactivate the current being supplied to the frame 110. The thermocouple 122 can comprise a platinum or stainless steel wire that can be welded between the frame 110 (e.g., at an anchor strut 206) and a conductive wire 116, where the electronic circuit 112 measures the difference in resistivity between the shape memory material and the thermocouple wire to determine the temperature of the frame 110. This can be calibrated and can have a linear temperature relationship.

The system 100 can include a thermoelectric cooling circuit 123 in electrical communication with the frame 110. The thermoelectric cooling circuit 123 can include, for example, a Peltier chip, disposed proximate the frame 110. As described above, when the frame 110 is cooled below the AF temperature, the shape memory material of the frame can transition back into the pliable, flexible martensite phase. This can be completed to capture the clot 40 in the frame 110. Instead of allowing the shape memory material to cool naturally, the thermoelectric cooling circuit 123 can pump heat from the frame 110 to cool the frame 110 more rapidly.

The frame 110 can be characterized by a plurality of struts 124 that can form closed cells 126, loops, or undulating patterns. A plurality of distal hoops or crown struts (which will be described below) can form the circumferential perimeter of the frame opening 128. The frame 110 can have a variety of shapes, including a low profile rounded tip, an open mouth funnel as shown, or other shapes that will be described herein. The plurality of struts 124 can be enclosed within a membrane 130. The membrane 130 can provide a means to direct fluid aspirate into the frame 110 and into the catheter 102. The membrane 130 can also maintain the position of the struts 124 when the frame 110 is in a collapsed configuration. Suitable membrane 130 materials can include elastic polyurethanes such as Chronoprene, Chronosil, Chronoflex, and other silicon and urethane polymers and the like that have high elasticity and insulative properties with good tear resistance. The membrane 130 can have a low hardness to enable the membrane 130 to stretch when the frame 110 is expanded. For example, the membrane 130 can have a Shore hardness typical of 00 ranges and Shore A0.1 to Shore A100 (e.g., Shore A40 to Shore A80). Because the membrane 130 is encapsulating the frame 110, which may be intended to expand, the membrane 130 can also have a degree of expandability, for example from 200-2200% (e.g., 400-800%).

The struts 124 can be coated with a film of material with high dielectric strength such as Parylene to insulate the struts from blood, which is a conductor, for example if the frame 110 is not fully encapsulated or sealed by the membrane 130.

Referring again to FIGS. 1C and 1D, the system 100 can be used in combination with an aspiration source 50. In many cases the expanded frame 110 can seal with the walls of the vessel 30 to direct aspiration to the distal end 108 of the catheter 102. In other words, the expanded frame 110 can also arrest flow and prevent the unwanted aspiration of blood proximal to the frame 110.

FIGS. 1C and 1D depict a system 100 wherein the catheter 102 for the frame 110 is inserted through an outer catheter 10. In some examples, however, the outer catheter 10 is not required. Instead the catheter 102 for the frame 110 can be the only catheter required to be advanced from a guide catheter (guide catheter not shown in FIG. 1C or 1D). The catheter 102 and frame 110, for example, can travel farther away from a guide catheter because the system is highly flexible and self-actuating (i.e., the frame 110 does not need to be unsheathed from a catheter to change from a closed configuration to an open configuration). Therefore, the guide catheter can reside in the internal carotid artery, for example, and catheter 102 and frame 110 can extend entirely to an M1 or M2 vessel.

Figure 2:
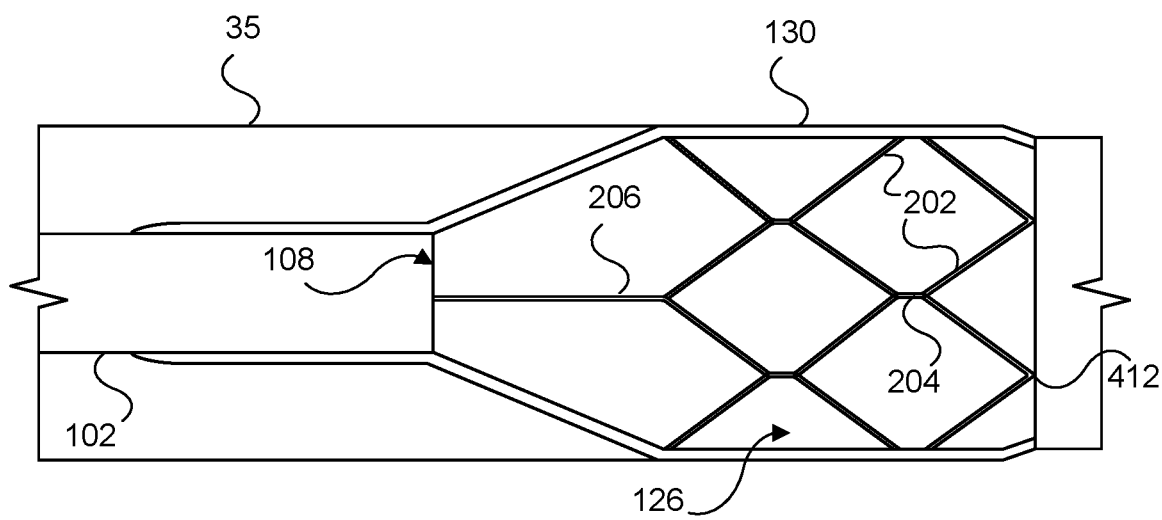
FIG. 2 is a cross-sectional view of an exemplary frame within a vessel, according to aspects of the present disclosure.

FIG. 2 is a cross-section illustration of an example funnel-shaped frame 110 in an expanded configuration. The length of the frame 110 can be longer or shorter than the one shown. The length can be increased, for example, to provide more surface-area contact with the vessel wall 35 or increase the reception space for a clot within the frame 110. The frame 110 can include a plurality of annular crowns 202 around the circumference of the frame 110. The annular crowns 202 can form the distal tip 412 of the frame 110 and/or provide radial support at any other location along the length of the frame 110. The frame 110 can include one or more longitudinal struts 204 that can connect peaks of the annular crowns 202. The annular crowns 202 and longitudinal struts 204 can form cells 126, or openings. The cells 126 can be spaced to promote even expansion of the frame 110 and membrane 130.

In some examples, the frame 110 does not include longitudinal struts 204, but instead the multiple annular crowns 202 can connected at each peak such that the cells 126 form a diamond-shaped lattice structure. Uniform spacing of the diamond-shaped cells 126 can also promote even expansion of the frame 110 and membrane 130. In yet other examples, the frame 110 does not include longitudinal struts 204, and the multiple annular crowns 202 are not connected at peaks. In these examples, the annular crowns 202 can instead be held into place by the membrane 130.

The shapes and configurations of the frame 110 described herein can be created by laser cutting the design into a tube. After laser cutting the design, the frame 110 can be positioned into its desired configuration and heat set such that the frame 110 can return to that desired configuration when heated during a procedure.

The frame 110 can include one or more anchor struts 206 extending proximally. The conductive wire 116 can be connected to the one or more anchor struts 206 to provide the current to the frame 110. As shown in FIG. 2, the membrane 130 can encapsulate at least a portion of the distal end 108 of the catheter 102.

The frame 110 can be kept short with minimal travel path (length of strut 124 and cross section, long length and large cross section will have greatest resistance) for current such that resistance is kept to a minimum so that the basket of the frame 110 can heat up and expand rapidly.

Figure 3A:
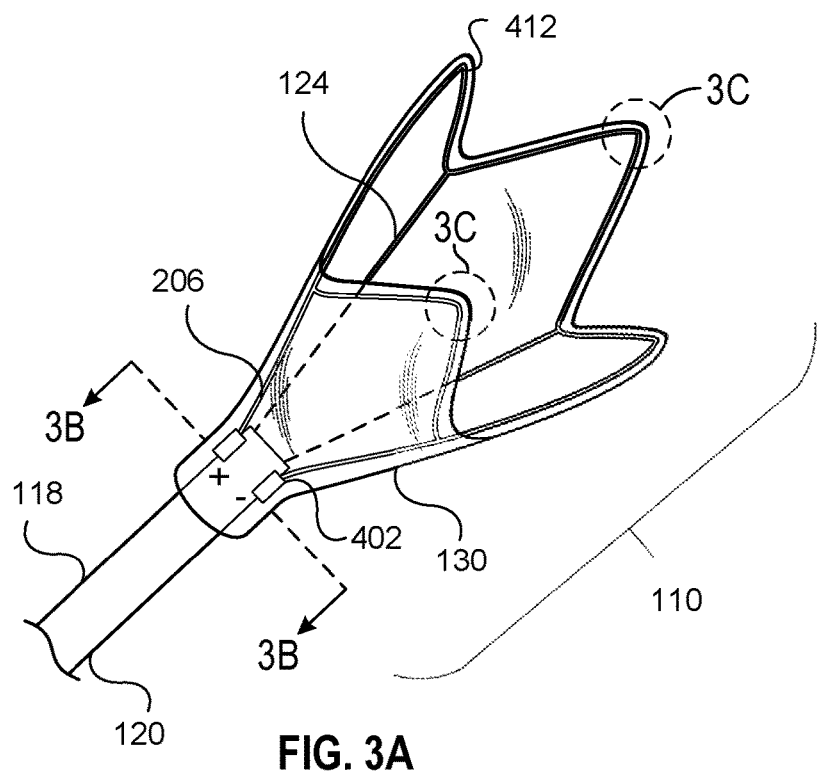
FIGS. 3A-3C are illustrations of exemplary designs for providing current to a frame, according to aspects of the present disclosure.
Figure 3B:
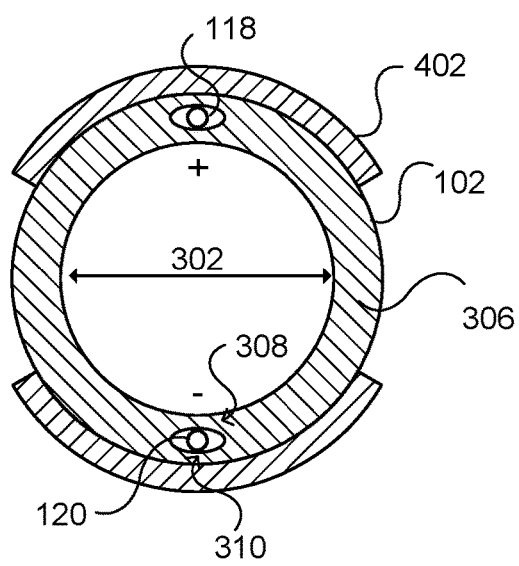
Figure 3C:
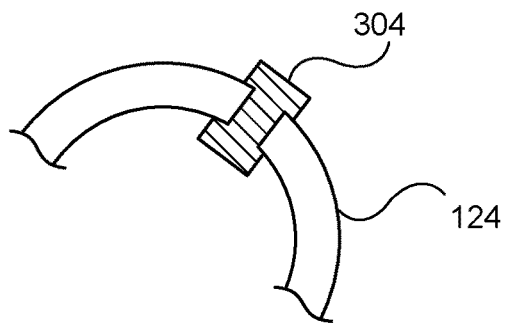

FIGS. 3A-3C depict an example design for providing current to a frame 110. As described above, one or more of the struts 124 defining the structure of the frame 110 can be anchor struts 206 that connect to a positive lead 118 or a negative lead 120 to receive current to heat the frame 110. The positive lead 118 and/or negative lead 120 can extend through the construction layers of the catheter 102 and connect with the anchor struts 206 within the construction layers. Embedding this electrical connection within the catheter 102 can prevent separation of the wires from the frame 110 and insulate from a conductive medium such as blood. In other examples, the positive lead 118, negative lead 120, and/or anchor struts 206 can be wound around the outer surface of the catheter 102 or within an inner lumen 302 of the catheter 102. The positive lead 118 and/or negative lead 120 can extend longitudinally along the length of the catheter 102 or in a spiral, weave, braid, or other pattern that may be used to improve stiffness or flexibility of the catheter 102 as desired. The profile of the wire can be varied longitudinally to fine tune stiffness/flexibility. In some examples, the anchor struts 206 can be pushed through openings formed in the catheter 102 wall.

Certain junctions between struts 124 can be connected with an insulating junction 304 such the current does not pass from one side of the insulating junction 304 to the other. This enables heat to be applied to the frame in a controlled pattern. Controlling the heat applied to different areas of the frame 110 enables certain portions of the frame to transition into an austenite phase while other portions do not transition. In some examples, as described above, insulating certain portions of the frame 110 also enables the frame 110 to have a distinct activation sequence. A first portion of the frame 110 can be configured to expand upon receiving current and a second portion of the frame can be configured to collapse upon receiving current. This can enable the user to collapse the frame 110 by applying a current to one portion of the frame 110 instead of waiting for the shape memory material to cool. Current can flow through a negative lead 120 into one side of a frame 110 and flow in an even electrical resistance path to the other side of the frame 110 where it returns through a positive lead 118. For example, if an anchor strut 206 of the frame 110 is connected to a v-shaped expansion strut of the frame 110, the anchor strut 206 can be approximately twice the cross-sectional area of each of the struts 124 that form the v-shaped expansion strut. This will allow for even flow of resistance between struts. Segments of the expansion frame can be divided by insulators and different segments can each have independent sets of positive and negative lead wires.

Figure 4A:
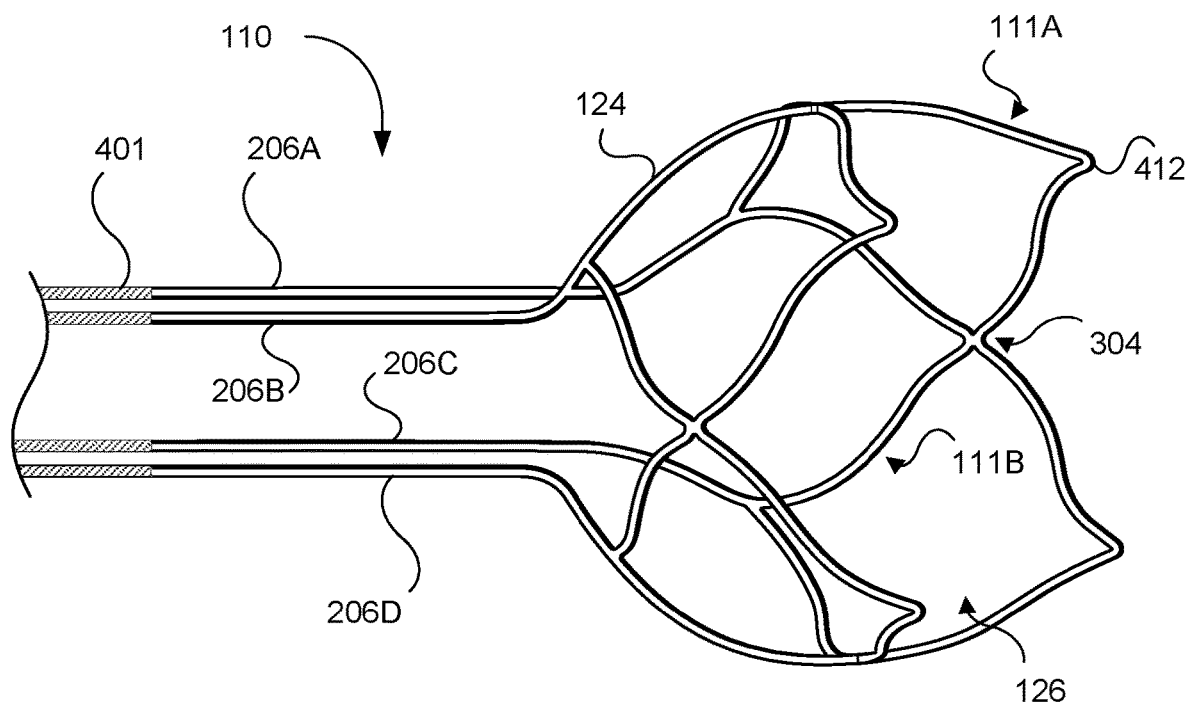
FIGS. 4A-4F are side-view illustrations of exemplary frame designs, according to aspects of the present disclosure.

FIGS. 4A-4F depict example designs for a frame 110. FIG. 4A illustrates a frame 110 having four anchor struts (i.e., anchor struts 206A,206B,206C,206D). As described above, the anchor struts 206A,206B,206C,206D can be embedded within the construction layers of the catheter 102 (catheter not shown in FIG. 4A). The individual anchor struts 206A,206B,206C,206D can have electrical connections 401 to different components of the system 100. In other words, the electrical connections 401 that are connected to the anchor struts 206A,206B,206C,206D can be connections to a positive lead 118, a negative lead 120, a thermocouple 122, a thermoelectrical cooling circuit 123, or any combination thereof. For example, two of the anchor struts 206A, 206B,206C,206D can be connected to a positive lead 118 and a negative lead 120 to provide current for heating the frame 110; and/or one of the anchor struts 206A,206B,206C, 206D can be connected to the thermocouple 122; and/or one of the anchor struts 206A,206B,206C,206D can be connected to the thermoelectric cooling circuit 123; and/or two anchor struts could be connected to a positive lead 118 and two anchor struts 206 to a negative lead 120; and/or any combination thereof. In some examples, two anchor struts can be connected to a positive lead 118 for more balanced flow of current through the frame 110 with two negative return leads.

In some examples, two of the anchor struts (e.g., anchor struts 206A and 206C) can connect to a positive lead 118 and a negative lead 120 for a first portion of the frame 110 (e.g., first portion 111A); and two of the anchor struts (e.g., anchor struts 206B and 206D) can connect to a positive lead 118 and a negative lead 120 for a second portion of the frame 110 (e.g., second portion 111B). This can enable the first portion 111A of the frame 110 to have a different activation characteristic than the second portion 111B of the frame 110. The first portion 111A of the frame 110 can be heat-set into an expanded configuration. By providing a current, and thus creating heat through resistance, the first portion 111A can expand during the procedure. The second portion 111B of the frame 110 can be heat-set into a collapsed configuration. By providing a current, and thus creating heat through resistance, the second portion 111B can collapse during the procedure. This enables a user of the system to advance the system 100 to the target site 20, direct a first current to the first portion 111A to expand frame 110, and aspirate the clot 40 into the frame 110. The user can then direct a second current to the second portion 111B to collapse the frame 110 and capture the clot 40. As is described above, the individual anchor struts 206A,206B,206C,206D can have electrical connections 401 to different components of the system 100. For examples with a first portion 111A and a second portion 111B, this means that two of the electrical connections 401 can include a second positive lead wire and a second negative lead wire, respectively, to heat one of the frame portions independently of the other, each circuit being insulated from the other.

The first portion 111A and second portion 111B of the frame 110 can comprise the same shape memory material and each material can have the same AF temperature. In other examples, the two portions can comprise the same material but have different AF temperatures. The first portion 111A and second portion 111B can comprise different shape memory materials, which can also enable the portions to have different AF temperatures, if needed. In examples having two portions with different AF temperatures, one portion can have an AF temperature below that of human blood (e.g., below 37° C.) such that it expands once delivered to the target site 20 and contacts blood; the other portion can have an AF temperature above 37° C. such that it only collapses upon being heated by a current. Conversely, one portion can have an AF temperature below that of human blood such that it collapses as it is heated by blood.

The first portion 111A and second portion 111B can be interconnected to form the cells 126 of the frame. When the first portion 111A and the second portion 111B of the frame 110 are intended to have different activation characteristics, heat from one portion can be shielded from the other portion by using an insulating junction 304 like the one shown in FIG. 3C. Instead of the first portion 111A and the second portion 111B being location at different sites of the frame 110, the first portion 111A and the second portion 111B can include two separate, coaxial frames that are not interconnected with one another. For example, the example frame 110 shown in FIG. 2 can have a second frame disposed over the frame shown in the figure that can circumferentially wrap around the inner frame. The outer frame (i.e., the outer portion) can be heat-set into a collapsed configuration and the inner frame (i.e., the inner portion) can be heat set to an expanded configuration. The inner frame can be expanded to receive the clot 40, and the outer frame can be activated to close, compress the inner frame, and capture the clot 40. In these examples, the inner and outer frame would be working against each other. In some examples, certain annular crowns 202 can have a different activation characteristic than other annular crowns 202, some expanding when heated while others collapsing when heated.

Figure 4B:
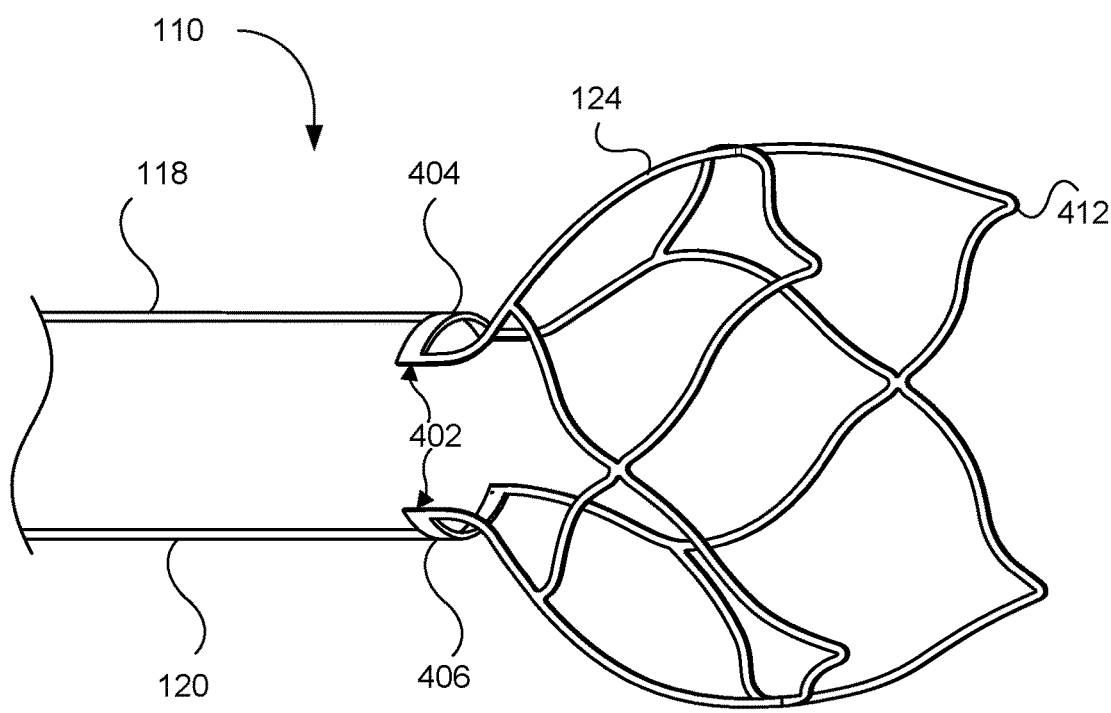
Figure 4C:
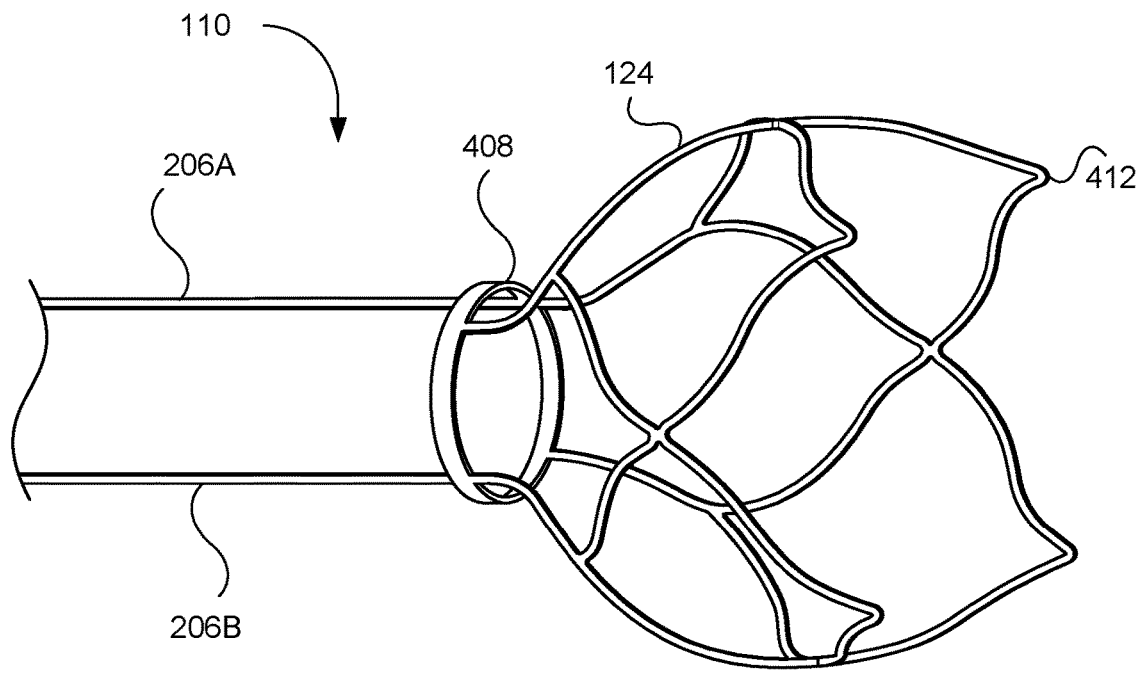

FIG. 4B illustrates a frame 110 having split collar 402. A first side 404 of the split collar 402 can be in electrical communication with a positive lead 118 while a second side 406 of the split collar 402 can be in electrical communication with a negative lead 120. The split collar 402 can provide a surface for the catheter 102 (catheter not shown in FIG. 4B) to lock with the frame 110. For example, the split collar 402 can be disposed within the construction layers of the catheter 102. In other examples, the split collar 402 can rest on the outer surface of the catheter 102, and the positive lead 118 and/or negative lead 120 can extend through a hole in the catheter 102 wall to connect to the split collar 402. The split collar 402 can also be disposed within the inner lumen 302 of the catheter 102. In other examples, the frame 110 can include a solid collar 408, as shown in FIG. 4C, which can be similar to the split collar 402. In the case of a solid collar 408, the positive lead 118 and/or negative lead 120 can be directly connected to the struts 124 so that the current is not overly resisted by the solid collar 408 leading to slow heating of the expansion frame.

Figure 4D:
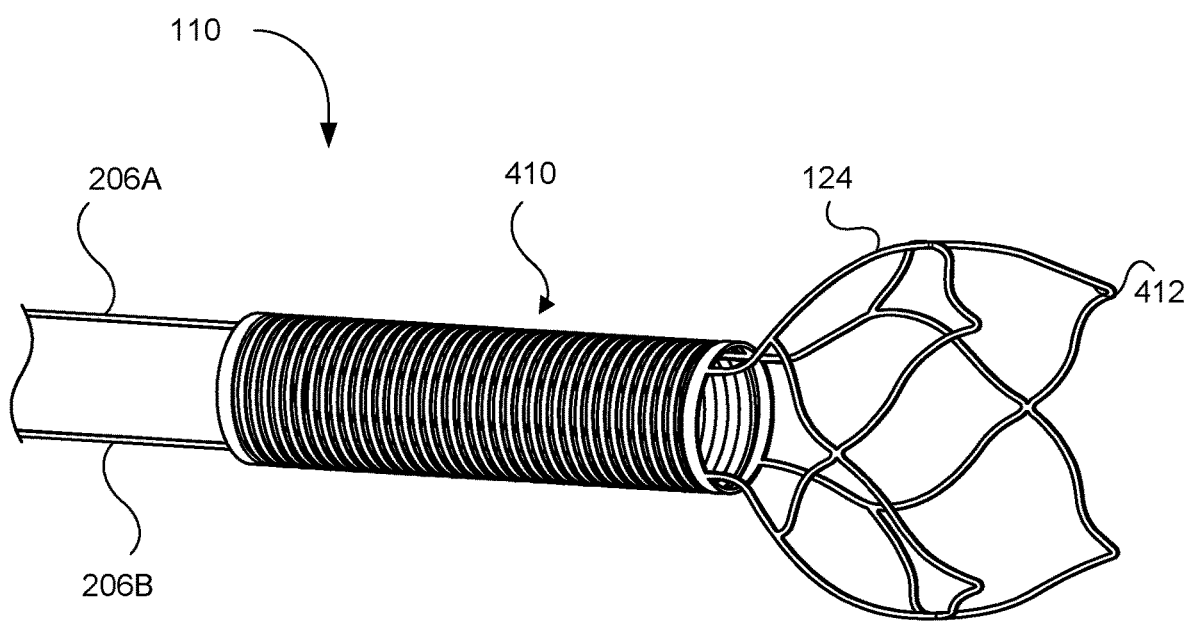

FIG. 4D illustrates a frame 110 with a coiled collar 410. The coiled collar 410 can be similar to the split collar 402 and/or solid collar 408 above in that it can be disposed within intermediate layers of the catheter 102, on the outer surface of the catheter 102, or within an inner lumen 302 of the catheter 102. The coiled collar 410 can provide pushability and flexibility while reducing complexity of construction to minimize wall thickness required at the distal end 108 of the catheter 102. The coiled collar 410 can be formed by the lead wires 116 or can be integral with the frame 110. Insulated lead wires of a highly conductive material (such as copper) can be braided to provide good pushability for the catheter construction. Stainless steel can also be used for the lead wires. While having less conductivity than copper, steel can offer better stiffness characteristics, and a larger diameter wire can be used to both counteract the lower conductivity while offering higher stiffness at the same time.

Figure 4E:
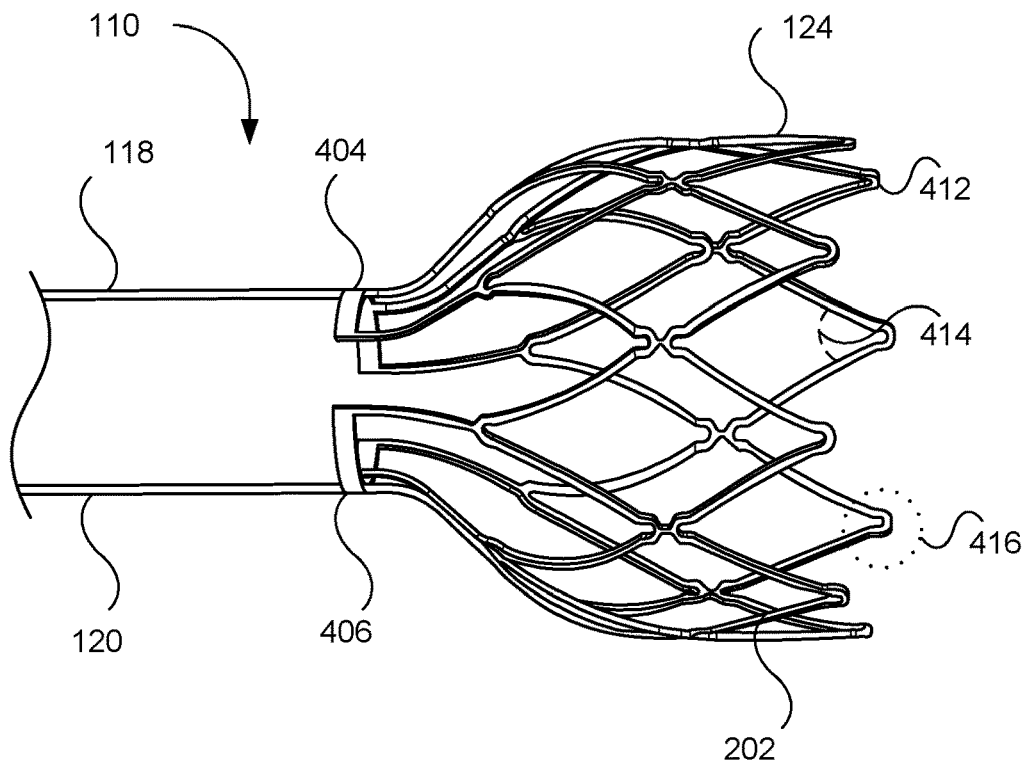
Figure 4F:
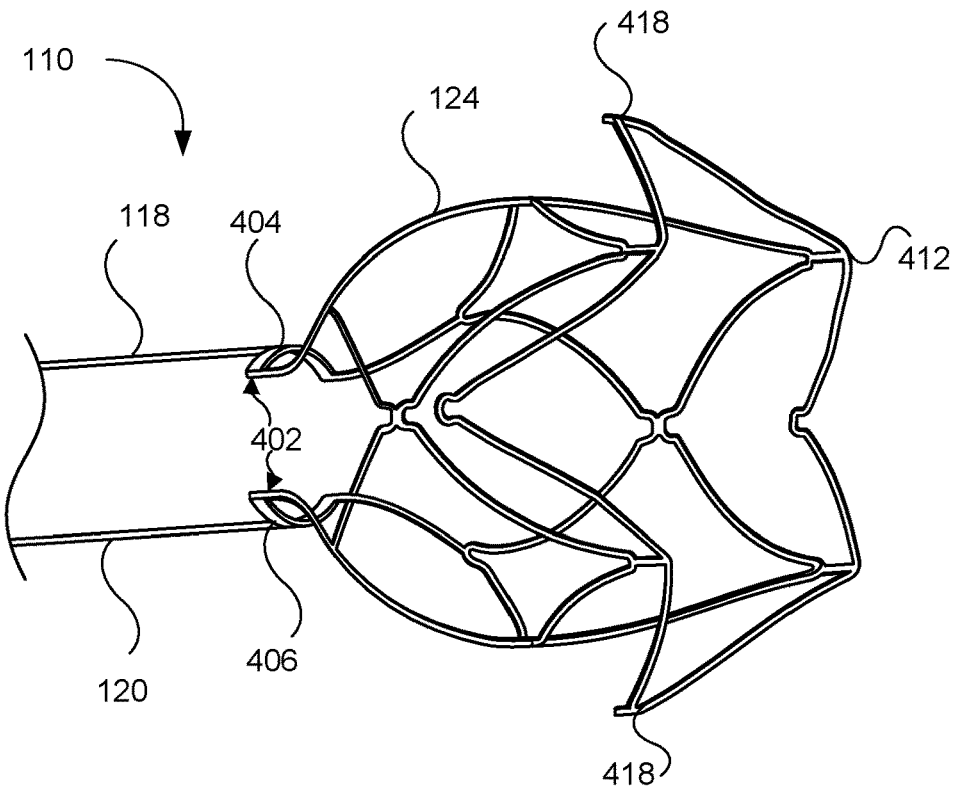

FIG. 4E illustrates an example strut 124 configuration for a frame 110. The axial force provided by the funnel-shaped frame 110 can be customized by changing the angles 414 between struts 124 (e.g., crown peaks 416). Acute angles offer less radial force and require less percentage elongation at break for the membrane 130, while obtuse angles offer more radial force and require more percentage elongation at break for the membrane 130. Acute angles can be achieved by lengthening struts 124 and/or increasing the number of crown peaks 416 per annular crown 202. Additionally, crown peaks 416 can be enlarged (i.e., rounded) to improve resistance to microcracks and fractures as the frame 110 expands. In another example, crown peaks 416 can form a large round curve extending substantially in a semi-circle from the proximal end of adjacent struts 124. Such large round semi-circular profiles will be atraumatic to a blood vessel As shown in FIGS. 4A-4D, a distal tip 412 of the frame 110 can taper or curve radially inwardly to decrease trauma to the vessel wall 35. In other examples, the distal tip 412 can be flared radially outward to improve apposition to the vessel wall 35. In some examples, the frame 110 can include wings 418 that extend proximal on the frame 110, as shown in FIG. 4F. By extending proximally, the wings 418 are less likely to puncture the vessel wall 35 if the frame 110 is advanced distally towards the target site 20. The wings 418 can extend outwardly beyond the other struts 124 of the frame 110 and further increase the radial force on the vessel wall 35. This configuration also enables the distal tip 412 to be flared inwardly to decrease the likelihood of trauma to the vessel wall 35 while also enabling the wings 418 to expand to contact the vessel wall 35 and create a fluid-tight seal in the vessel 30. In another example, the crowns of the wings 418 can be connected to a proximal strut, as described below with reference to FIGS. 5A and 5B.

Figure 5A:
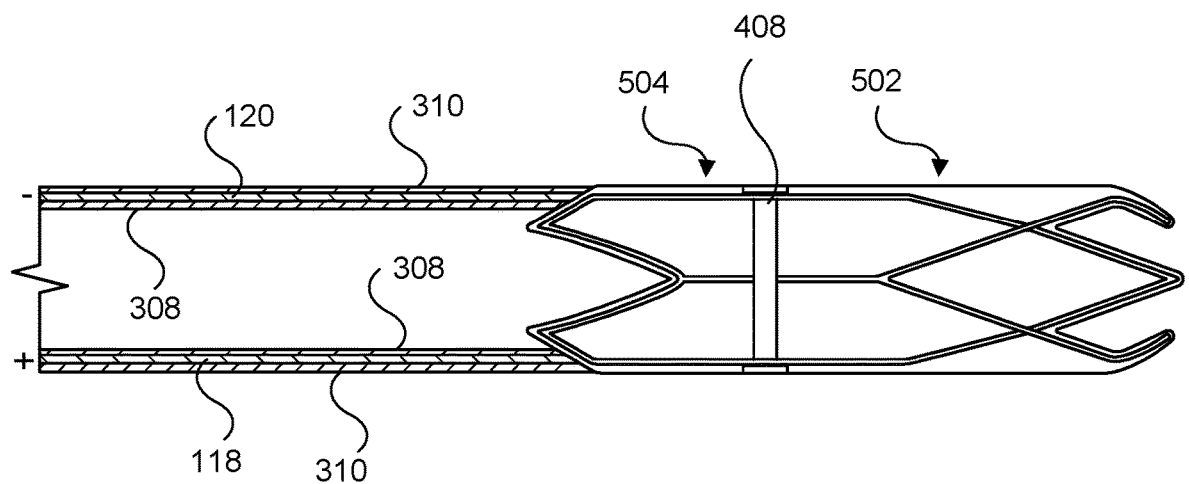
FIGS. 5A and 5B are illustrations of an exemplary frame having opposing funnels, according to aspects of the present disclosure.
Figure 5B:
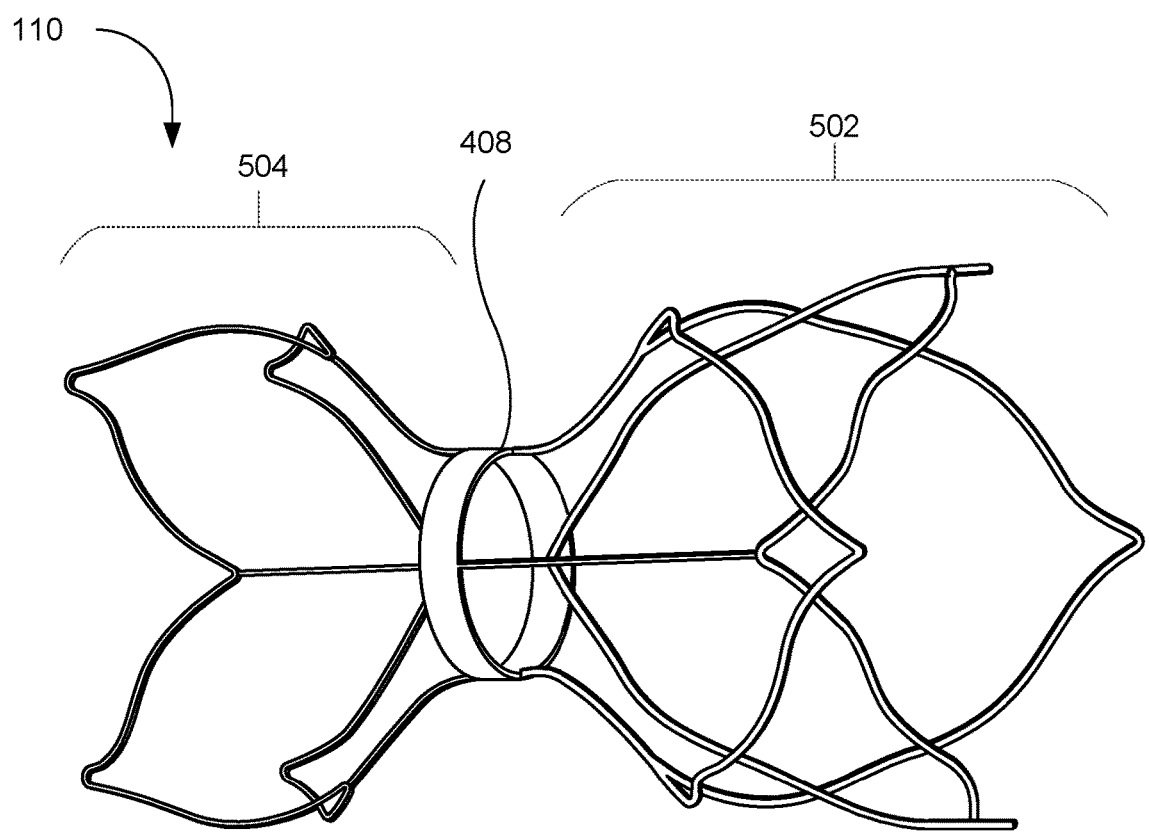

FIGS. 5A and 5B depict an example frame 110 having a distal portion 502 and a proximal portion 504. The distal portion 502 of the frame 110 can be similar to any of the frames 110 described herein. The proximal portion 504 can oppose the distal portion 502 and be directed toward a catheter hub (catheter hub not shown in FIG. 5A or 5B). The proximal portion 504 can have an expanded configuration and an open configuration, similar to the configurations described for any of the frame 110 embodiments described above. In a collapsed configuration, the proximal portion 504 can rest upon or adjacent to the distal end 108 of the catheter 102. Once opened into its expanded configuration, the proximal portion 504 can create a proximal-facing funnel to counteract blood pressure/blood flow and prevent the unwanted aspiration of blood proximal to the frame 110. The proximal portion 504 and/or distal portion 502 can include a membrane 130. The proximal portion 504 and distal portion 502 can be connected with a solid collar 408 or any of the other collars described herein. In some examples, the proximal portion 504 and distal portion 502 can be connected to different conductive wires such that one portion can be opened or closed with a first current and one portion can be opened or closed with a second current, as described above. In another example, struts 124 can extend proximally from the proximal crowns of the proximal portion to a second collar positioned proximally of the solid collar 408. Either or both collars can be segmented. Connecting the proximal peaks of the proximal portion to a proximal collar can aid in reducing the likelihood of the frame snagging on an outer guide sheath or vessel side branch as it is retracted proximally.

Figure 6:
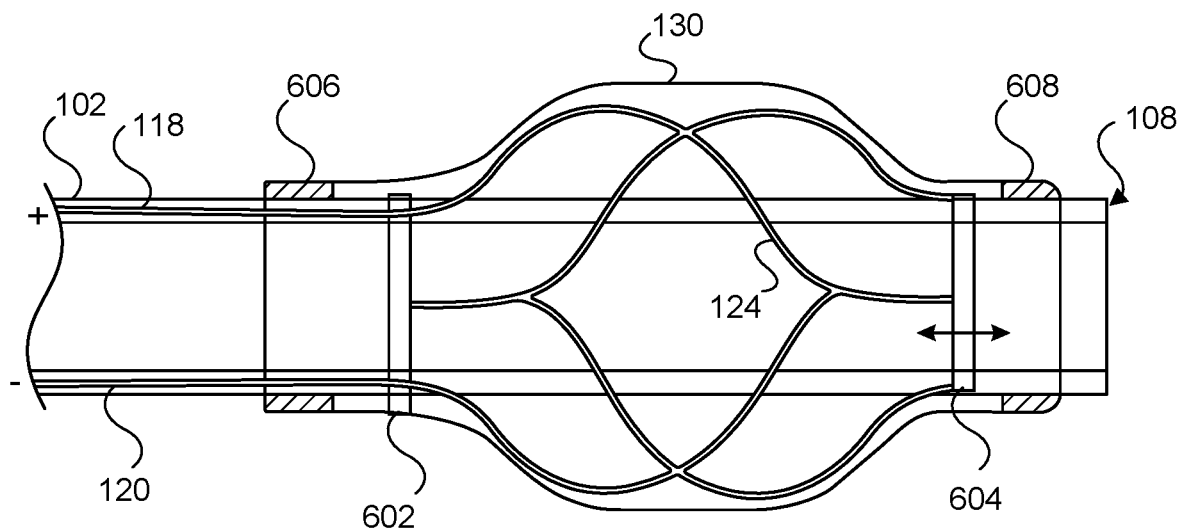
FIG. 6 is a cross-sectional illustration of an exemplary balloon-shaped frame, according to aspects of the present disclosure.

FIG. 6 illustrates a design for a system 100 that enables the frame 110 to act as a closed balloon. The frame 110 can be positioned along the length of the catheter 102 proximate the distal end 108 of the catheter 102. Unlike many of the designs described herein, the frame 110 does not extend beyond the distal end 108 of the catheter 102 in this example. The frame 110 can include a fixed collar 602 at one end and a floating collar 604 at the other end. The fixed collar 602 can be connected to the outer surface or can be embedded within the construction layers of the catheter 102 such that it does not slide along the length of the catheter 102; the floating collar 604 can, conversely, slide along the length of the catheter 102. The plurality of struts 124 can be connected to both collars 602,604 and extend between the two. In some examples, the struts 124 can be integral struts (as shown in FIG. 6), while in other examples the struts can be overlapping (e.g., a weave pattern). When a current is applied to the frame 110, the frame 110 can expand, and the floating collar 604 can contract towards the fixed collar 602. As the floating collar 604 contracts, the struts 124 expand and force the membrane 130 balloon to expand outwardly to create a seal against the vessel wall 35. When the shape memory material cools, the frame 110 can then collapse under the compression force exerted by the expanded elastomeric balloon. The frame 110 can float inside the balloon material or the frame 110 can be encapsulated in the balloon material. In some examples, the membrane 130 can include a first seal 606 and a second seal 608 at the ends of the membrane 130. The first seal 606 and/or second seal 608 can create a fluid-tight junction between the membrane 130 and the catheter 102. The first seal 606 and/or second seal 608 can be permanently fixed to the catheter 102, and the membrane 130 can stretch as the struts 124 expand. In other examples, one of the first seal 606 and/or second seal 608 can contract along with the floating collar 604. In these cases, the first seal 606 and/or second seal 608 can be a gasket, like an O-ring, that can slide along the outer surface of the catheter 102.

Figure 7:
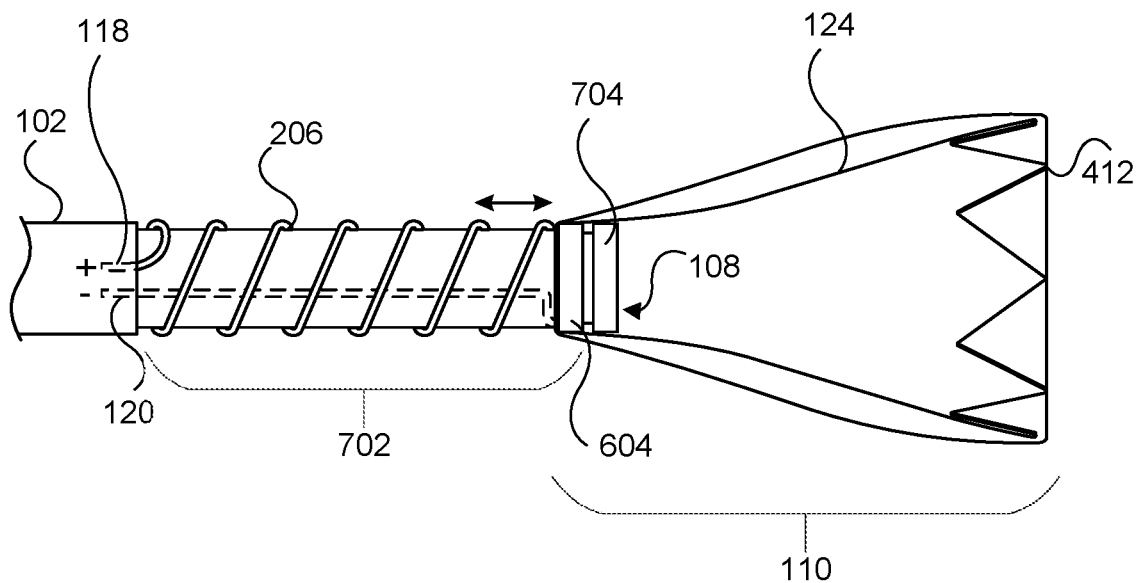
FIG. 7 is a side-view illustration of an exemplary actuated clot retrieval system having a retractable frame, according to aspects of the present disclosure.

FIG. 7 illustrates a design for a system 100 that enables an anchor strut 206 to expand or contract as a spring, thereby moving the position of the frame 110 along the catheter 102. The end of the catheter 102 proximal the frame 110 can include a narrow section 702. An anchor strut 206 extending from the frame 110 can coil around the narrow section 702. The anchor strut 206 can be connected at one end to a floating collar 604 that can move along the length of the narrow section 702. The opposite end of the anchor strut 206 can be connected to a conductive wire 116 (e.g., a positive lead 118 or a negative lead 120). The anchor strut 206 can be heat-set in a collapsed configuration such that, as the anchor strut 206 is heated, it contracts to pull the frame 110 proximal along the catheter 102. The distal end 108 of the catheter 102 can include a catheter tip 704 having an outer diameter larger than an inner diameter of the floating collar 604. The catheter tip 704 can prevent the frame 110 from sliding off of the catheter 102 distally. This mechanism enables the distal tip 412 of the frame 110 to be aligned with the distal end 108 of the catheter 102 when the anchor strut 206 is fully contracted. In some examples, the anchor strut 206 can be contracted and the frame 110 expanded while fluid is aspirated into the catheter 102. Once the clot is pulled proximal to the distal end 108 of the catheter 102, the anchor strut 206 can be returned to an extended configuration, and, simultaneously, the frame 110 can collapse around the clot for removal from the vessel. The anchor strut 206 and the frame 110 can be heated by the same current (i.e., by the same positive lead 118 and negative lead 120), or the anchor strut 206 and the frame 110 can include separate electrical connections such that they can be heated independently. The distal end 412 can be advanced in the collapsed configuration through activation of the anchor strut 206, which acts as a linear movement actuator, so that the tip 412 is closer to the clot, and the tip 412 can be actuated to seal the vessel prior to aspiration.

In an alternative embodiment, the distal end 108 of the catheter 102 itself can instead be actuated by a springing mechanism. For example, the catheter 102 can include a flexible portion that includes a shape memory material disposed therein. As the shape memory material in the catheter 102 expands with heat, the distal end 108 of the catheter 102 can extend through the funnel formed by the frame 110 and towards the clot.

Figure 8A:
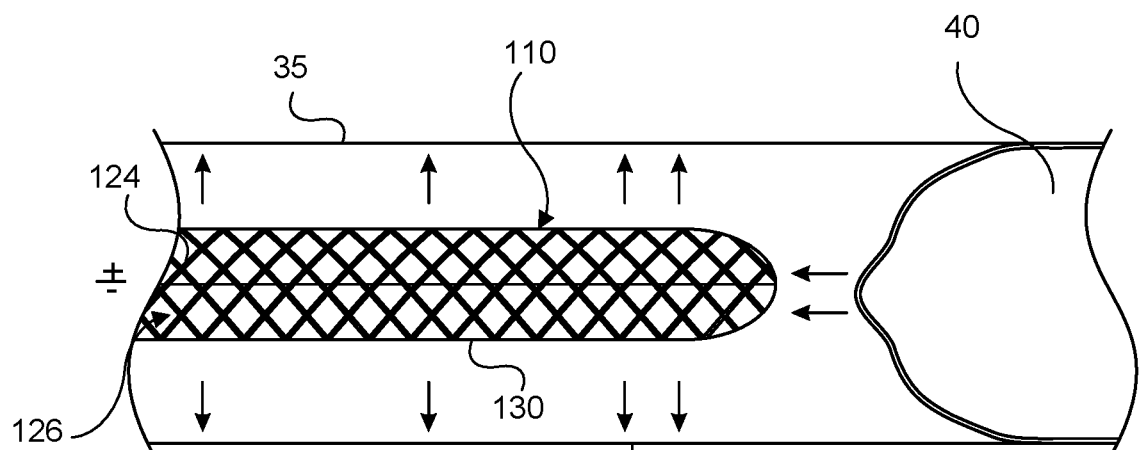
FIGS. 8A and 8B are cross-sectional illustrations of exemplary designs to expand the bore size of a catheter, according to aspects of the present disclosure.
Figure 8B:
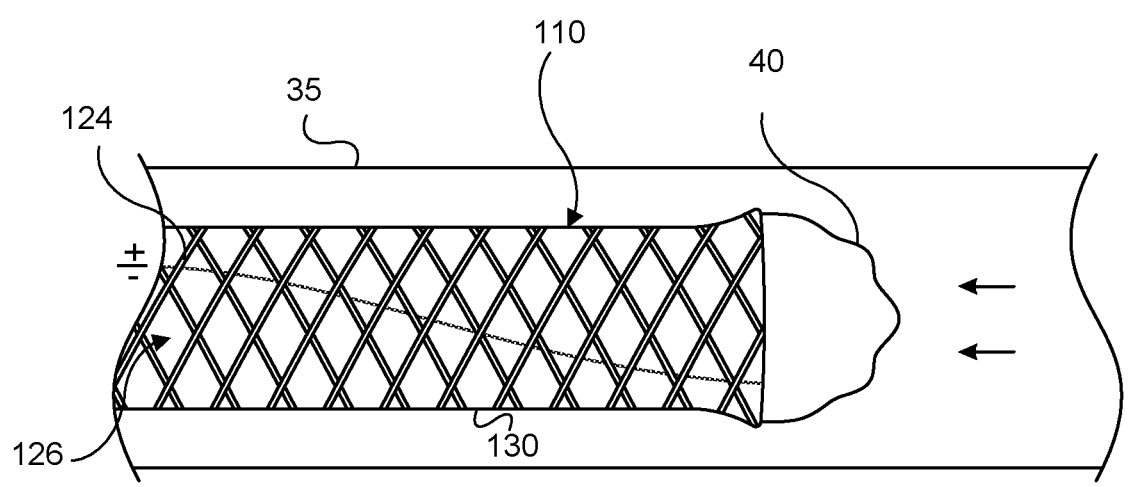

FIGS. 8A-8B illustrate a design for a system 100 that enables the frame 110 to adjust the bore size of the catheter 102. The frame 110 can extend from the distal end 108 of the catheter 102 (catheter not shown in the figure) to form the distal-most portion of the catheter 102. When the catheter 102 reaches the clot 40, the frame 110 can expand to increase the bore size of the catheter 102 and thus increase the flow into the catheter 102. This can be especially beneficial for larger or stiffer clots. For example, as the catheter 102 aspirates the clot, if the clot is resisting being pulled into the catheter, the operator can supply the current to the frame 110 to increase the flow into the catheter 102. The frame 110 can be a laser cut lattice design, a shape set wire design, a wire braid design, and/or the like. The frame 110 can be covered with a membrane 130, as described above. The frame 110 can also be designed to expand for the full length of the catheter 102.

In some examples, instead of extending from the catheter 102, the frame 110 can be positioned within an inner lumen 302 of the catheter 102. In a similar manner, as the frame 110 expands inside the inner lumen 302, the bore size of the catheter 102 can increase to adjust the flow.

Figure 9A:
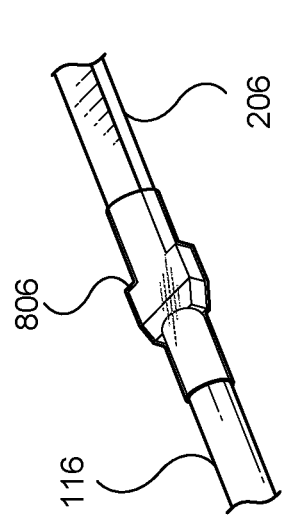
FIGS. 9A-9F are illustrations of exemplary attachments to connect an anchor strut to a shape memory material, according to aspects of the present disclosure.
Figure 9B:
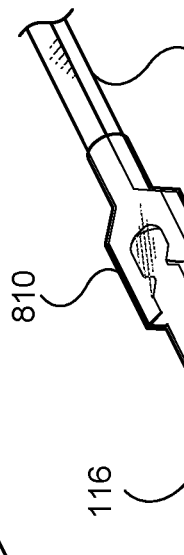
Figure 9C:
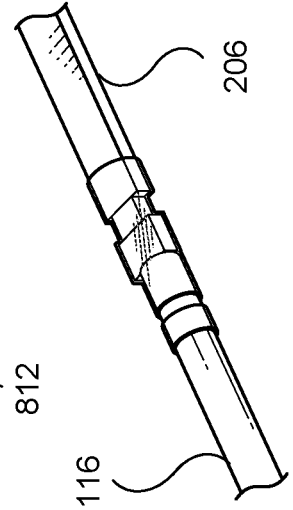
Figure 9D:
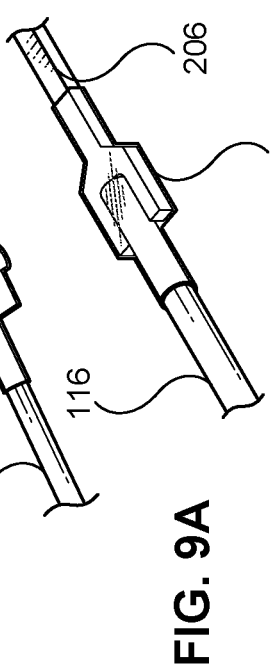
Figure 9E:
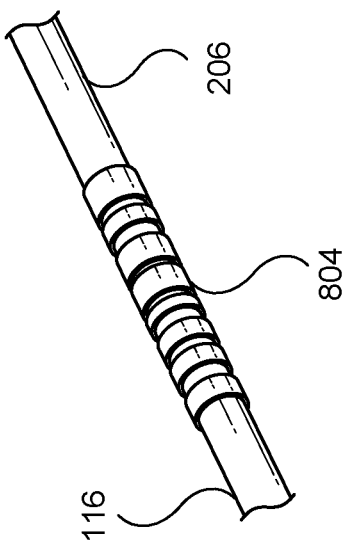
Figure 9F:
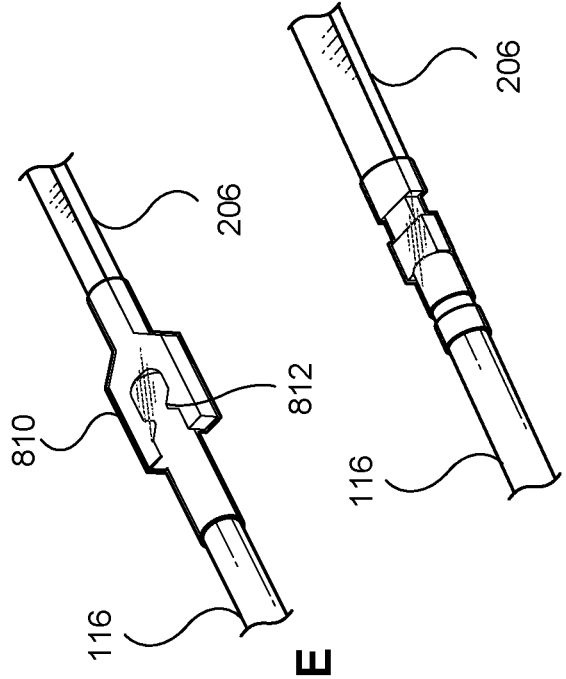

FIGS. 9A-9F depict example designs for attaching the conductive wire 116 to the anchor strut 206 of the frame 110. The conductive wire 116 can be connected to the anchor strut 206 by a variety of mechanical means. FIG. 9A depicts a mechanical connector 802 that includes a "T" connection at one end and a hook at the other end, the hook grabbing and holding the "T" connection. FIG. 9B depicts a coiled connector 804. A third material can be coiled over the conductive wire 116 and the anchor strut 206 to create the electrical connection. FIG. 9C depicts a mechanical crimp 806. The crimp 806 can include a third material that crimps the conductive wire 116 at one end and the anchor strut 206 at the other end. FIG. 9D depicts a forked crimp 808. One end of either the conductive wire 116 or the anchor strut 206 can include a fork that can be crimped upon the other end of the connection. FIG. 9E is an alternative forked crimp 810 including teeth 812 that can assist in gripping the material between the forks. FIG. 9F depicts a heat shrink method of bonding the conductive wire 116 and the anchor strut 206. Other examples for connecting the conductive wire 116 to the anchor strut 206 include, but are not limited to, over-moulding, soldering, adhering, or welding the two components. Adhesives for adhering conductive wires 116 to shape memory materials can include cyanoacrylate and epoxy. Welding methods for bonding the conductive wires 116 to shape memory materials include, for example laser, welding, plasma welding, tungsten inert gas (TIG) welding, and the like.

Figure 10:
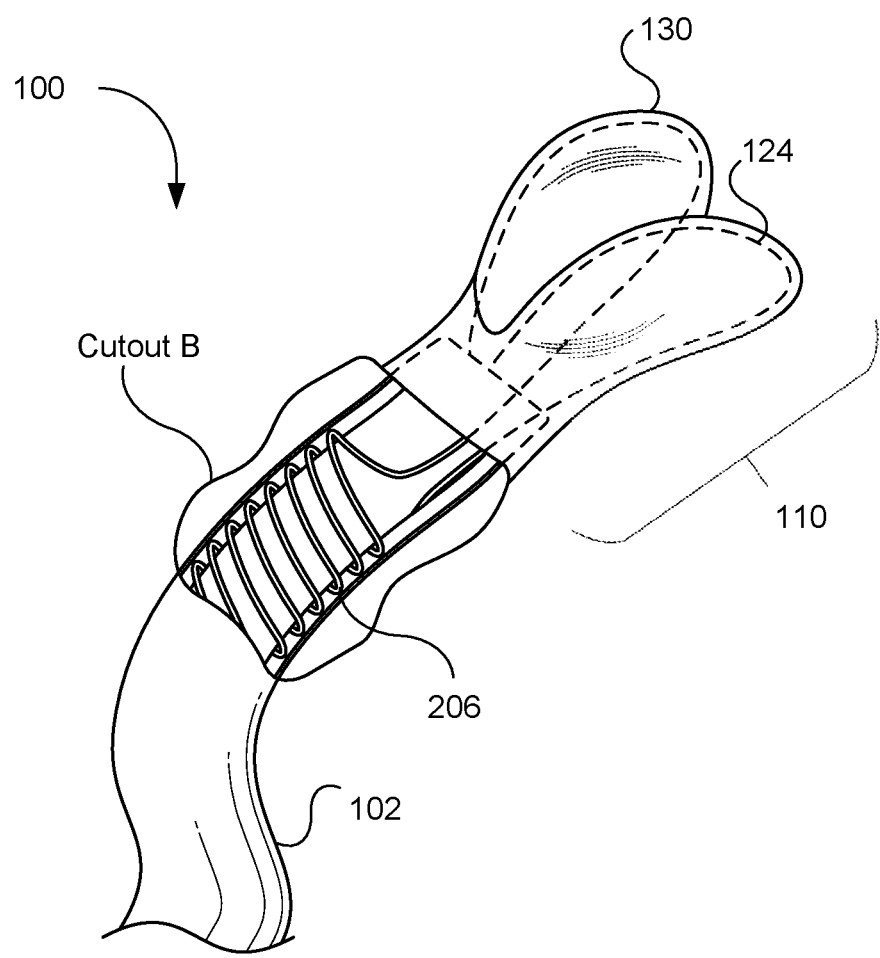
FIG. 10 is an illustration of an exemplary actuated clot retrieval system having a glove-shaped frame, according to aspects of the present disclosure.

FIG. 10 depicts an example system 100 with a frame 110 that opens like a glove. As can be seen, it is not required that the frame comprise a plurality of cells 126. The frame 110 can instead include a simple loop of the struts 124 that can open like a glove when heated. FIG. 10 also shows that, in some examples, the leads 118,120 and/or anchor struts 206 can spiral within construction layers of the catheter 102, as shown in cutaway B. Spiraling the anchor struts 206 can increase the length of, and thus the electrical resistance of, the shape memory material, which can increase the heat supplied to the frame 110. In another example, to conserve energy, the anchor struts 206 can be kept short and the leads can be configured straight to reduce the effect of inductance from a coil. In another embodiment, the frame 110 can be supplied as a number of simple loops each heated independently from a single lead pair or from a set of lead pairs.

Figure 11:
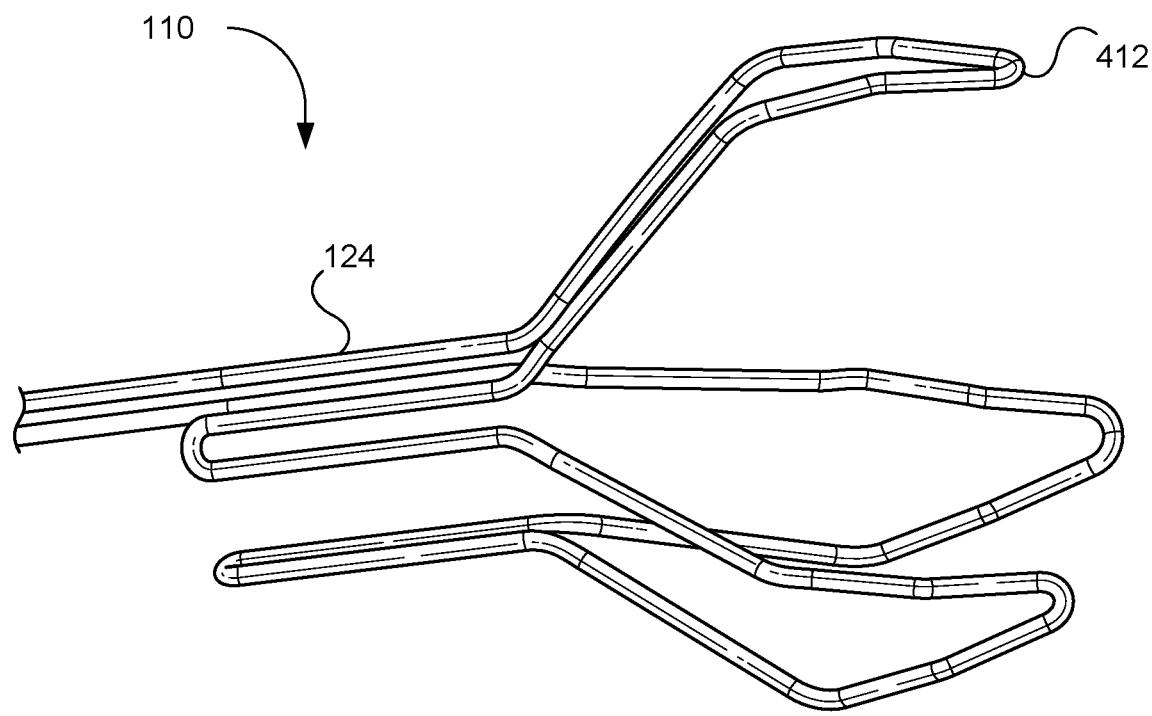
FIG. 11 is a side-view illustration of an exemplary frame design, according to aspects of the present disclosure.

FIG. 11 depicts a frame 110 having a distal tip 412 turned slightly inward in an expanded configuration. Turning the distal tip 412 radially inwardly can create an atraumatic profile should the user inadvertently push the device distally during use. The feature can also aid in grasping a fibrin rich clot 40 for safe extraction from a vessel 30.

Figure 12:
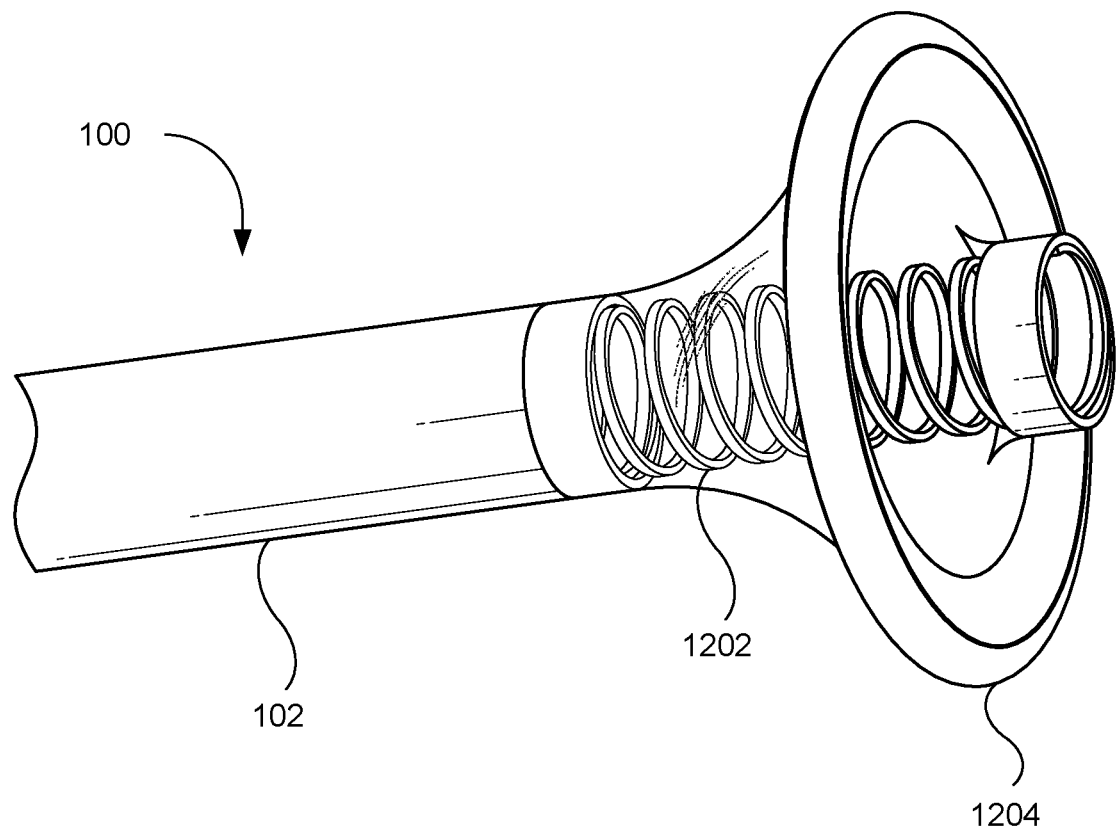
FIG. 12 is an illustration of an exemplary frame having a retractable distal spring, according to aspects of the present disclosure.

FIG. 12 depicts a frame 110 having a distal spring 1202. The distal spring 1202 can contract upon heating. The contracting distal spring can deform a distal collar membrane 1204, which expands outwardly through inversion to create a funnel shape. The distal collar membrane 1204 can comprise a stiffer material than other membranes 130 described above such that the distal collar membrane 1204 can expand radially when it is contracted with the distal spring 1202. The distal collar 1204 can be a composite of a braid and a membrane or a braid and a fine weave mesh, the braid acting as a reinforcement to promote inversion.

Figure 13A:
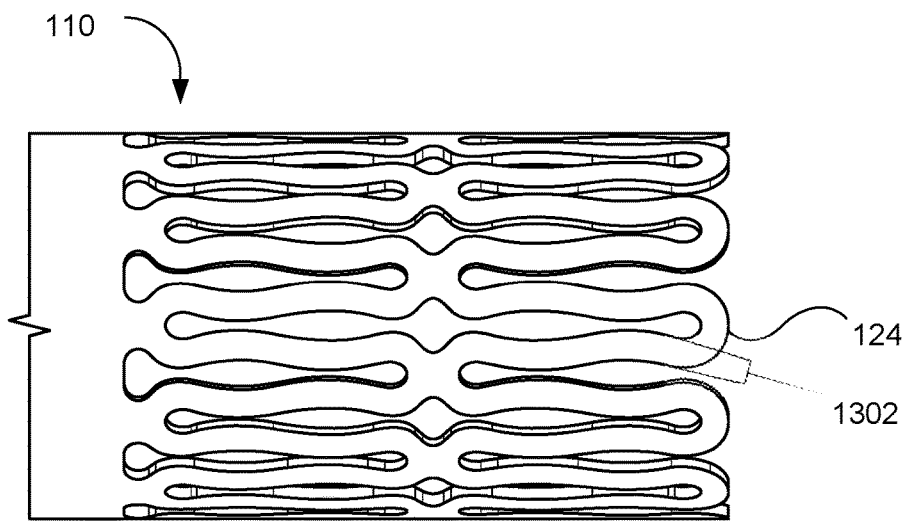
FIGS. 13A and 13B depict a frame having struts with a constant cross sectional area, according to aspects of the present disclosure.
Figure 13B:
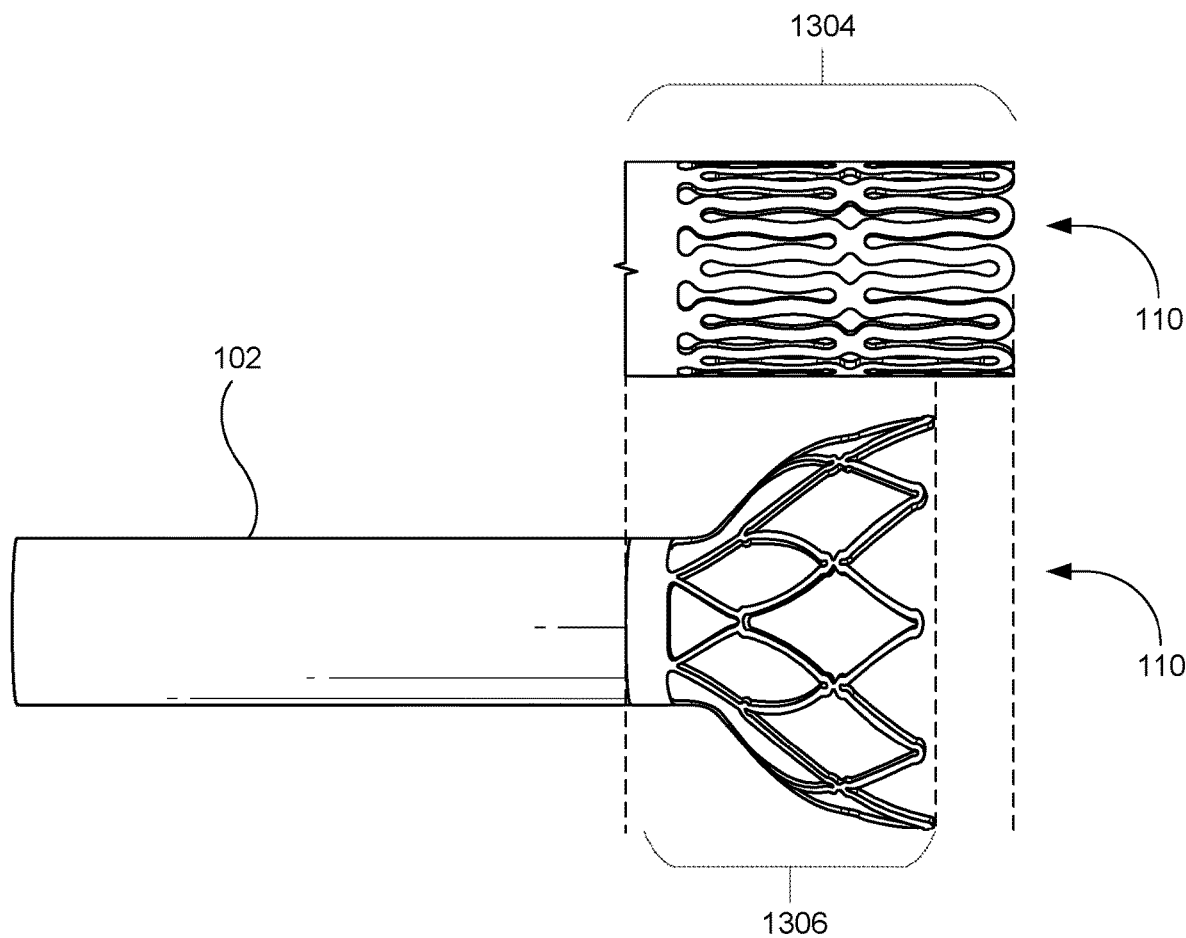

FIGS. 13A and 13B depict a frame 110 having struts 124 with a constant cross sectional area 1302. The constant cross section area 1302 can enable even transfer of current across the entirety of the frame 110. As shown in FIG. 13B, the example design also enables the frame 110 to decrease slightly in length as the frame 110 transitions from a closed configuration to an open configuration. In a closed configuration, the frame 110 can have a first length 1304, and as current is provided, and heat is created through resistance, the frame 110 can open like a funnel with a shorter, second length 1306.

Figure 14A:
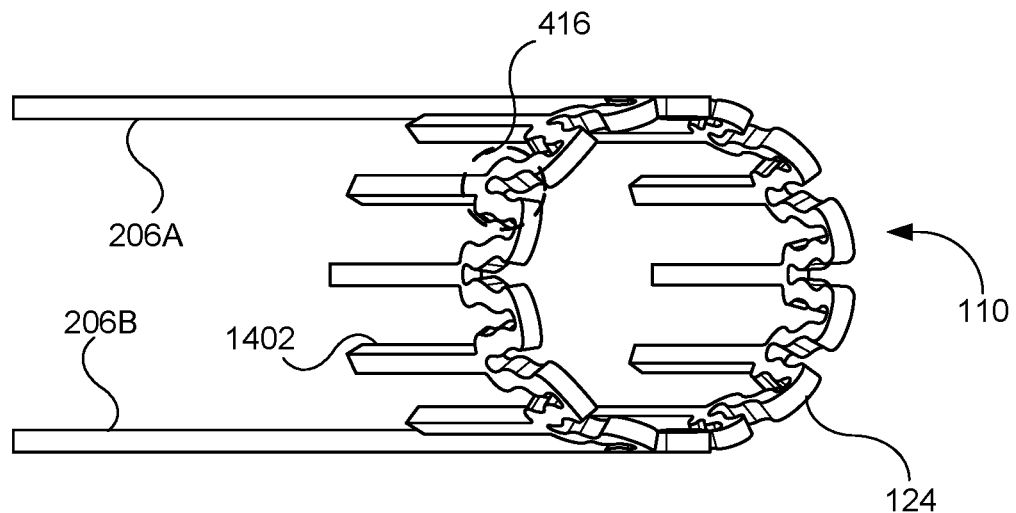
FIGS. 14A and 14B depict a frame having struts that split into a v-shape for even flow of heat/electrical resistance, according to aspects of the present disclosure.
Figure 14B:
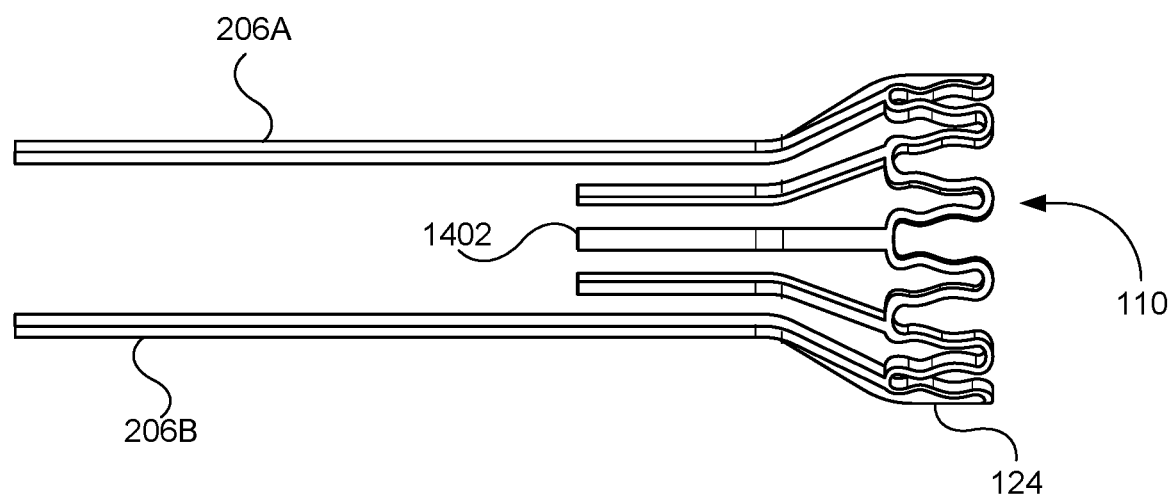

FIGS. 14A and 14B depict a frame 110 having struts 124 that split into a v-shape for even flow of heat/electrical resistance. A frame 110 can also include dissipation struts 1402 positioned at crown peaks 416 that can remove heat from the struts 124 (e.g., to allow the struts 124 to cool) and also provide support for a membrane 130 cover. The design can also enable the frame 110 to decrease slightly in length as the frame 110 transitions from a closed configuration to an open configuration, as described above with reference to FIGS. 13A and 13B.

Figure 15:
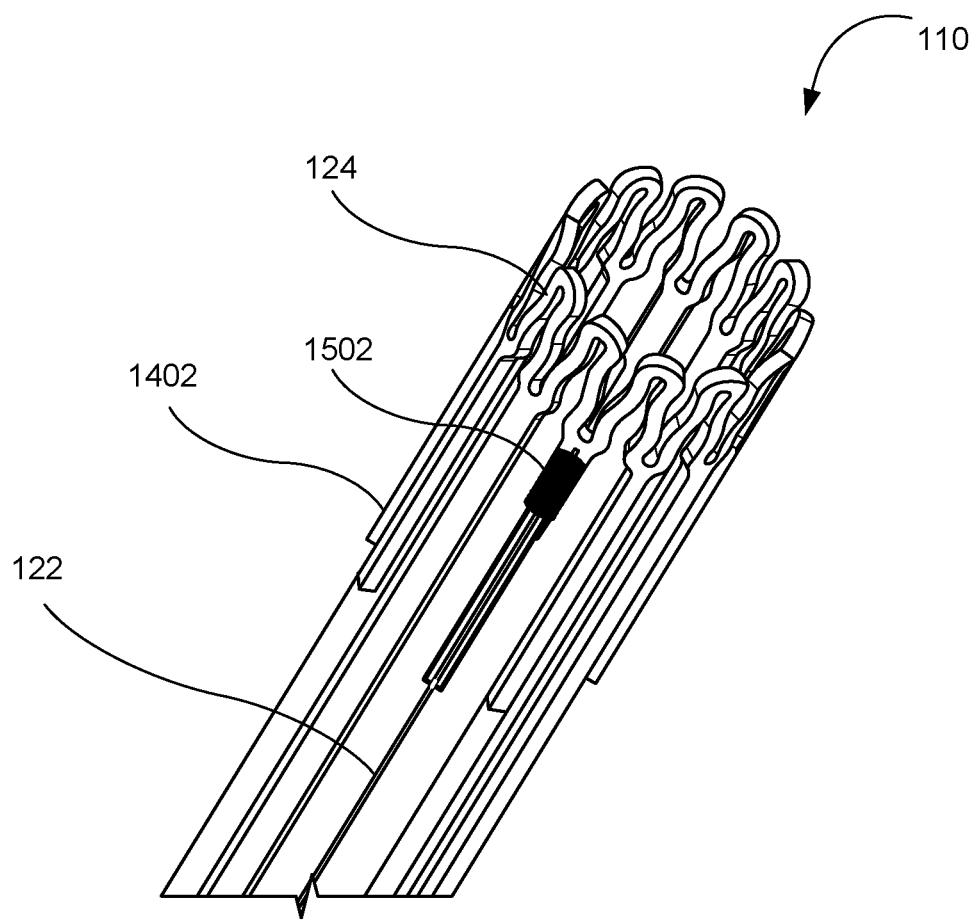
FIG. 15 is a perspective view of an example frame having a thermocouple wire connected to a dissipation strut, according to aspects of the present disclosure.

FIG. 15 is a perspective view of an example frame 110 having a thermocouple 122 that is a wire connected to a dissipation strut 1402. The thermocouple 122 wire can include a material such as platinum or stainless steel can be attached to the frame 110 at an attachment 1502. The attachment 1502 can include a weld or adhesive. The thermocouple 122 wire can be in electrical communication with the electronic circuit 112, and the electronic circuit 112 can measure the difference in resistivity between the frame 110 material and the thermocouple 122 to determine the temperature of the frame 110. This can be calibrated and can have a linear temperature relationship.

Figure 16:
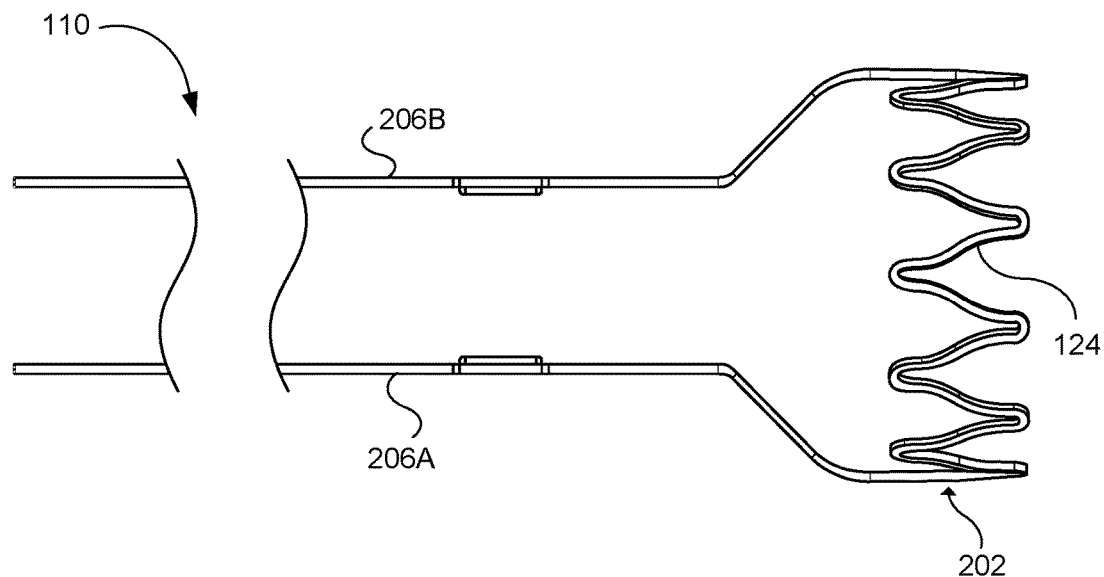

FIGS. 16-18B depict example designs for a frame 110. FIG. 16 depicts an example frame 110 having no collar (e.g., neither a split collar 402 nor a solid collar 408). A first anchor strut 206A and a second anchor strut 206B can extend from a frame 110 having a single annular crown 202. The single annular crown 202 can be held in place by a membrane 130 (not shown in FIG. 16).

Figures 17A, 17B:
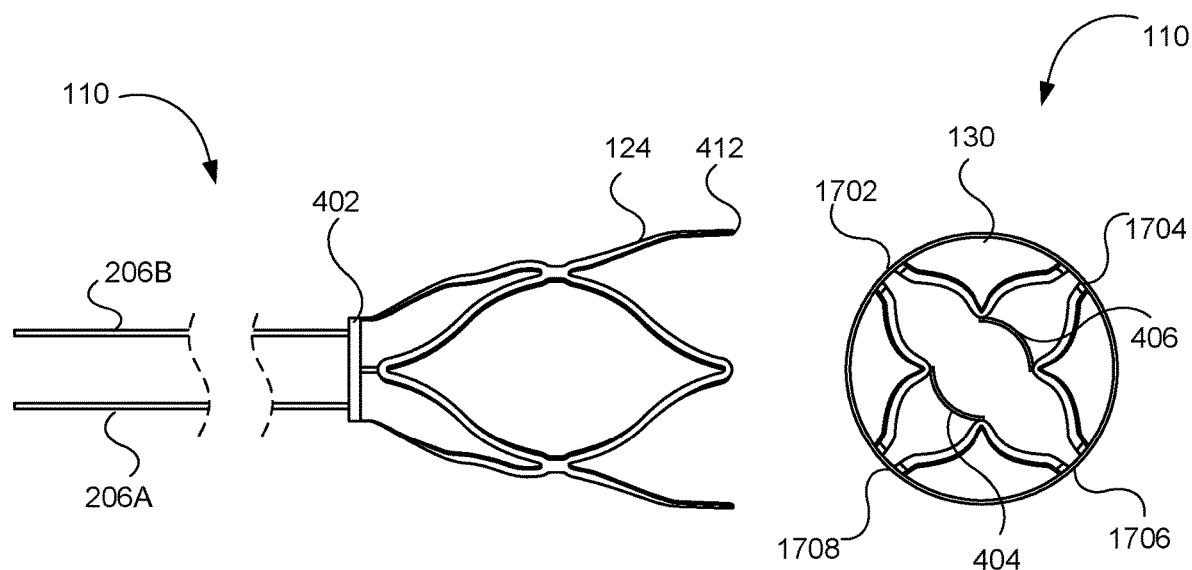

FIGS. 17A and 17B depict an example frame 110 having a split collar 402. The distal tip 412 of the frame 110 can open to four distinct points (e.g., points 1702, 1704, 1706, 1708), as shown in the end view of FIG. 17B. The frame 110 can include a membrane 130 to encapsulate the distal tip 412 of the frame 110 and connect the points 1702, 1704, 1706, 1708 into a rounded funnel shape.

FIGS. 18A and 18B depict an example frame 110 having a plurality of distal points 1802. The frame 110 can include a membrane 130 to encapsulate the distal tip 412 of the frame 110 and connect the plurality of distal points 1802 into a rounded funnel shape, as shown in the end view of FIG. 18B.

Figure 19:
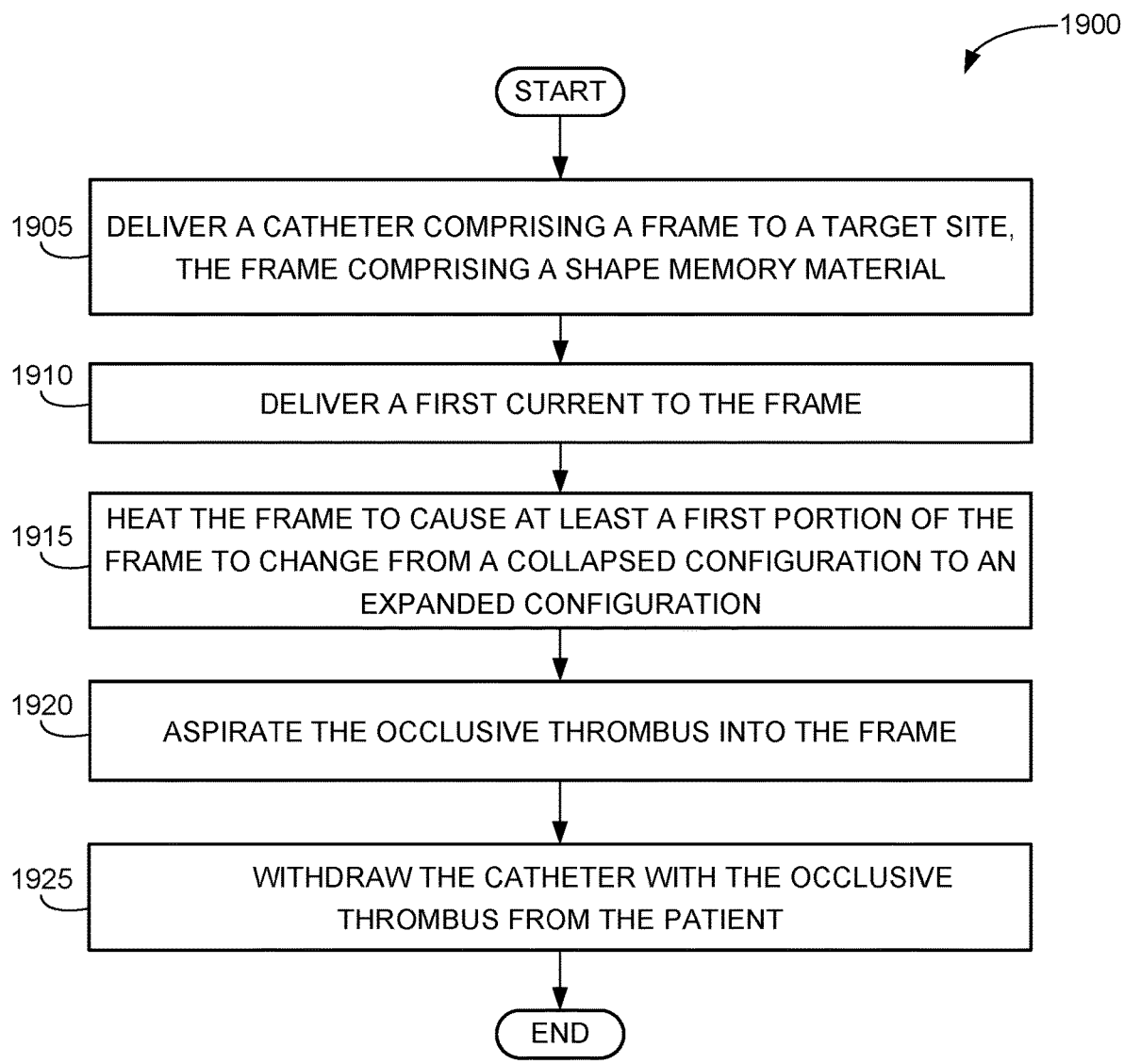
FIG. 19 is a flow diagram illustrating a method of retrieving an occlusive thrombus from a blood vessel of a patient, according to aspects of the present disclosure.

FIG. 19 is a flow diagram illustrating a method of retrieving an occlusive thrombus from a blood vessel of a patient. The method steps in FIG. 19 can be implemented by any of the example means described herein or by similar means, as will be appreciated. Referring to method 1900 as outlined in FIG. 19, in step 1905, a catheter can be delivered to a target site. The catheter can be advanced, for example, through an outer catheter or access sheath. The catheter can comprise a frame manufactured from a shape memory material. The frame can have a funnel shape, can be disposed within an inner lumen of the catheter, can be disposed along the length of the catheter, or can have any of the other shapes described herein.

In step 1910, method 1900 can include delivering a first current to the frame. The first current can be delivered through a conductive wire connecting the frame to an electronic circuit. The user can activate the electronic circuit outside of the patient.

In step 1915, method 1900 can include heating the frame to cause at least a first portion of the frame to change from a collapsed configuration to an expanded configuration. The heating of the frame is caused by the electrical resistance of the shape memory material as the current runs through the frame. At least a first portion of the frame means the entire frame can expand, though it is not necessary that the entire frame expands. As described above, the frame can have multiple portions with different transformation characteristics. For example, a first portion of the frame can be heated to expand while a second portion is not heated. The second portion, for example, can be heated in a later step to capture the thrombus. A shape memory funnel frame can be restricted from expanding by an electrically actuated member, removing the electric current allows the restraining member to release and the shape memory material expands from the heat of blood.

At step 1920, method 1900 can include aspirating the occlusive thrombus into the frame. The aspiration can be directed into the catheter by the frame, which can include a membrane covering that directs fluid.

At step 1920, method 1900 can include withdrawing the catheter with the occlusive thrombus from the patient. With the thrombus captured within the frame, the thrombus can be pulled from the vessel of the patient without worry of the thrombus dislodging from the catheter due to poor capture.

Method 1900 can end after step 1925. In other embodiments, additional steps according to the examples described above can be performed. For example, method 1900 can include deactivating the first current to cool the at least a first portion of the frame. Cooling the shape memory material can cause the at least a first portion to collapse upon the occlusive thrombus to improve the capture the thrombus for removal.

In some examples, method 1900 can include delivering a second current to at least a second portion of the frame. The second portion can have a different transformation characteristic than the first portion. For example, the second portion can be pre-set into a collapsed configuration in its austenite phase, which means that, once heated, it can collapse upon the thrombus. Accordingly, method 1900 can include heating, via the second current, the second portion of the frame to cause the second portion of the frame to change from an expanded configuration to a collapsed configuration and upon the occlusive thrombus.

Method 1900 can also include cooling the at least a first portion of the frame with a thermoelectric cooling circuit to cause the at least a first portion of the frame to collapse upon the occlusive thrombus. A thermoelectric cooling circuit, such as a Peltier chip, can pump heat from a system. Using this effect, the thermoelectric cooling circuit can cause the at least a first portion of the frame to cool and collapse more rapidly around the occlusive thrombus.

Method 1900 can include delivering the current in a series of pulses so as to maintain a steady frame temperature, and the electronic circuit can monitor the temperature and adjust the pulse duration and/or length accordingly.

Method 1900 can also include monitoring a temperature of the frame with a thermocouple. In some examples, the thermocouple can monitor to determine if the frame exceeds a certain temperature, for example 50° C., and deactivate the first current if the frame exceeds the temperature.

Figure 20:
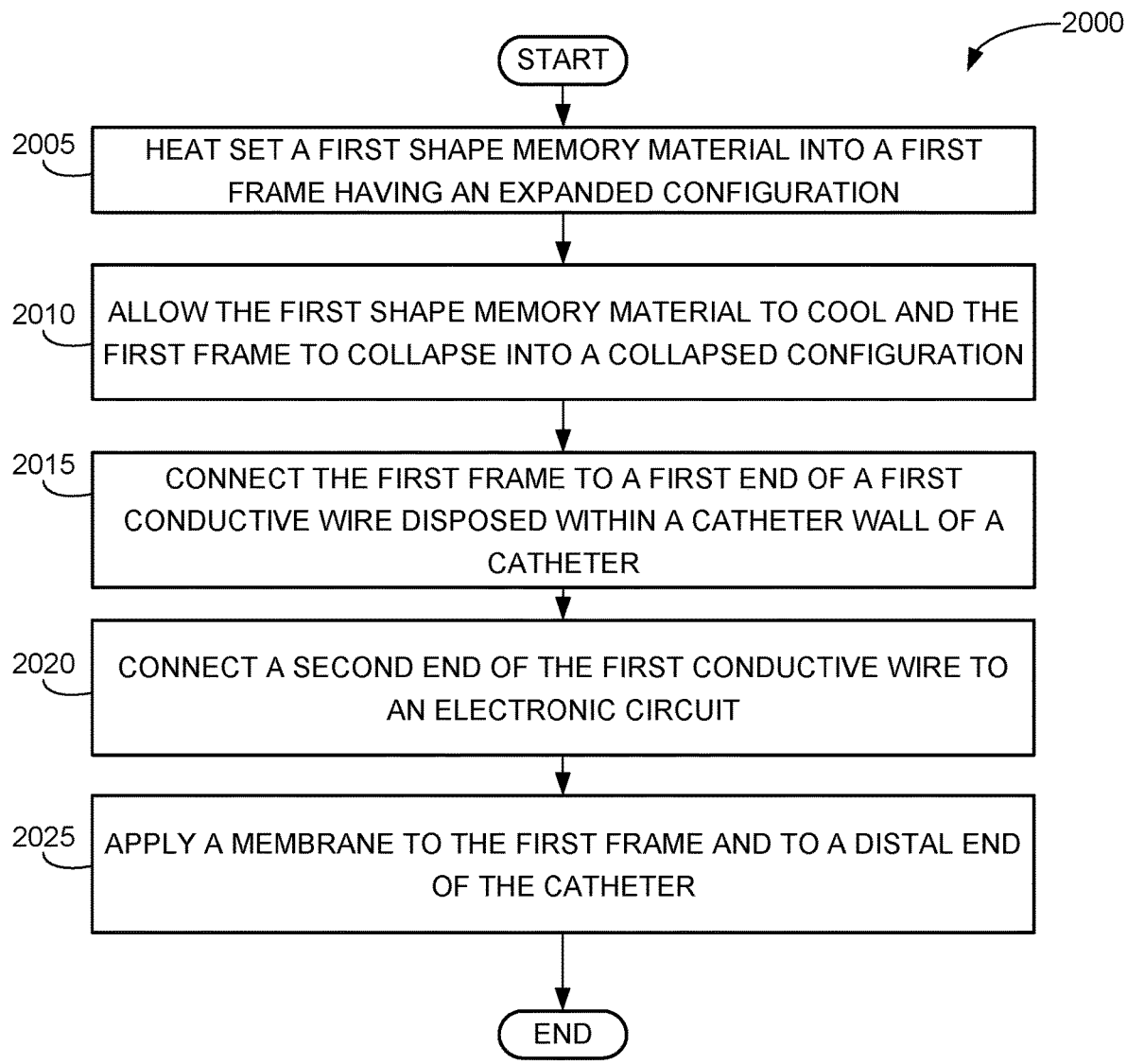
FIG. 20 is a flow diagram illustrating a method of manufacturing an exemplary actuated clot retrieval system, according to aspects of the present disclosure.

FIG. 20 is a flow diagram illustrating a method of manufacturing an exemplary actuated clot retrieval system. The method steps in FIG. 20 can be implemented by any of the example means described herein or by similar means, as will be appreciated. Referring to method 2000 as outlined in FIG. 20, in step 2005, a first shape memory material can be heat set into a first frame having an expanded configuration. As described throughout this disclosure, heat setting the shape memory material can include heating the frame to above its AF temperature, forming the frame into a desired shape, and then allowing the frame to cool.

In step 2010, method 2000 can include allowing the first shape memory material to cool and the frame to collapse into a collapsed configuration. Once cooled, the frame is more flexible and pliable, as it is in its martensite phase. The collapsed frame can return to its predetermined shape by reheating the frame to above the AF temperature.

In step 2015, method 2000 can include connecting the first frame to a first end of a first conductive wire disposed within a wall of a catheter (e.g. catheter wall 306 of FIG. 3). The frame can have an electrical connection, for example, to a positive and a negative lead to provide current to heat the frame. This electrical connection can be made within the construction layers of the catheter itself, thereby protecting the connection from inadvertent separation. The electrical connection can be made within the construction layers by providing a first catheter layer (e.g., first layer 308 in FIG. 3) and then disposing the first conductive wire on the first catheter layer. At this point, the frame can be attached to the conductive wire, for example by attaching the conductive wire to an anchor strut of the frame. A second catheter layer (e.g., second layer 310 in FIG. 3) can be applied over the first conductive wire and the first anchor strut to encapsulate the connection in the construction layers of the catheter.

In step 2020, method 2000 can include connecting a second end of the first conductive wire to an electronic circuit. The electronic circuit can be positioned distal to the frame. The electronic circuit can be disposed within a housing that includes a switch to activate the current.

In step 2025, method 2000 can include applying a membrane to the first frame and to a distal end of the catheter. The membrane can be applied by a variety of methods. One method is to apply a thin base layer of material to a dipping mandrel with the catheter in place, followed by injection molding an intermediate layer with collapsed frame held in place by an outer mold, and a final top layer can be applied using a second outer mold or through a final dip coating process. In some examples, a preformed ring of a material that will not form a bond with the encapsulation membrane can be used to hold the frame in a collapsed position. After sufficient material has encapsulated the frame through a dipping or molding process, the preformed ring can be removed before a final dipping or molding process to fill in the void left by the ring. Alternatively, a preformed ring of the same material can be used to avoid the necessity to remove the ring.

Method 2000 can end after step 2025. In other embodiments, additional steps according to the examples described above can be performed. For example, method 2000 can include heat setting a second shape memory material into a second frame having a collapsed configuration. The second frame can be heat set in a similar manner as described above for the first frame. The second frame can be heat set into a collapsed configuration such that, once heated, the second frame can return to the collapsed configuration (e.g., to capture a clot). Method 2000 can include allowing the second shape memory material to cool and then connecting the second frame to a first end of a second conductive wire disposed within the catheter wall. Method 2000 can include connecting a second end of the second conductive wire to the electronic circuit so that the second frame can receive a current. The membrane can be applied to the second frame in a similar manner to the method described for the first frame. The first shape memory material and the second shape memory material can be the same alloys or can be different alloys. Providing different alloys can enable the two frames to have different transformation characteristics (e.g., they can transform from martensite to austenite phases at different temperatures). The first frame and the second frame can be coaxial and connected to the distal end of the catheter. In this manner, the first frame can expand when heated, and the second frame can collapse upon the first frame to capture the clot when heated.

The descriptions contained herein are examples of embodiments of the disclosure and are not intended in any way to limit the scope of the disclosure. As described herein, the disclosure contemplates many variations and modifications of the aspiration device including using alternative geometries of structural elements, combining shapes and structural elements from various example embodiments, using alternative materials, etc. These modifications would be apparent to those having ordinary skill in the art to which this disclosure relates and are intended to be within the scope of the claims which follow.

The invention claimed is:

1. A system for retrieving an obstruction in a blood vessel, the system comprising:
   a catheter;
   a first conductive wire;
   an electronic circuit providing a first current to the first conductive wire;
   a frame in electrical communication with the first conductive wire and comprising a shape memory material, at least a first portion of the frame being expandable from a collapsed configuration to an expanded configuration upon being heated by the first current; and
   a thermoelectric cooling circuit in electrical communication with the frame,
   wherein the at least a first portion of the frame is collapsible from the expanded configuration to the collapsed configuration upon removal of heat by the thermoelectric cooling circuit.

2. The system of claim 1, wherein the shape memory material has a transition temperature of from approximately 45° C. to 55° C.

3. The system of claim 1, wherein at least a second portion of the frame is collapsible from an open configuration to a collapsed configuration upon being heated.

4. The system of claim 3, further comprising a second conductive wire in electrical communication with the second portion of the frame, the second conductive wire receiving a second current from the electronic circuit.

5. The system of claim 4, further comprising an insulating junction connecting the first portion of the frame to the second portion of the frame, such that the first current does not reach the second portion of the frame and the second current does not reach the first portion of the frame.

6. The system of claim 1, further comprising a membrane cover disposed around the frame.

7. The system of claim 1, wherein the frame is disposed within an inner lumen of the catheter.

8. The system of claim 1, further comprising a thermocouple in electrical communication with the frame.

9. The system of claim 1, wherein:
   the shape memory material is in a martensite phase when the at least a first portion of the frame is in the collapsed configuration; and
   the shape memory material is in an austenite phase when the at least a first portion of the frame is in the expanded configuration.

* * * * *